Figure 1:
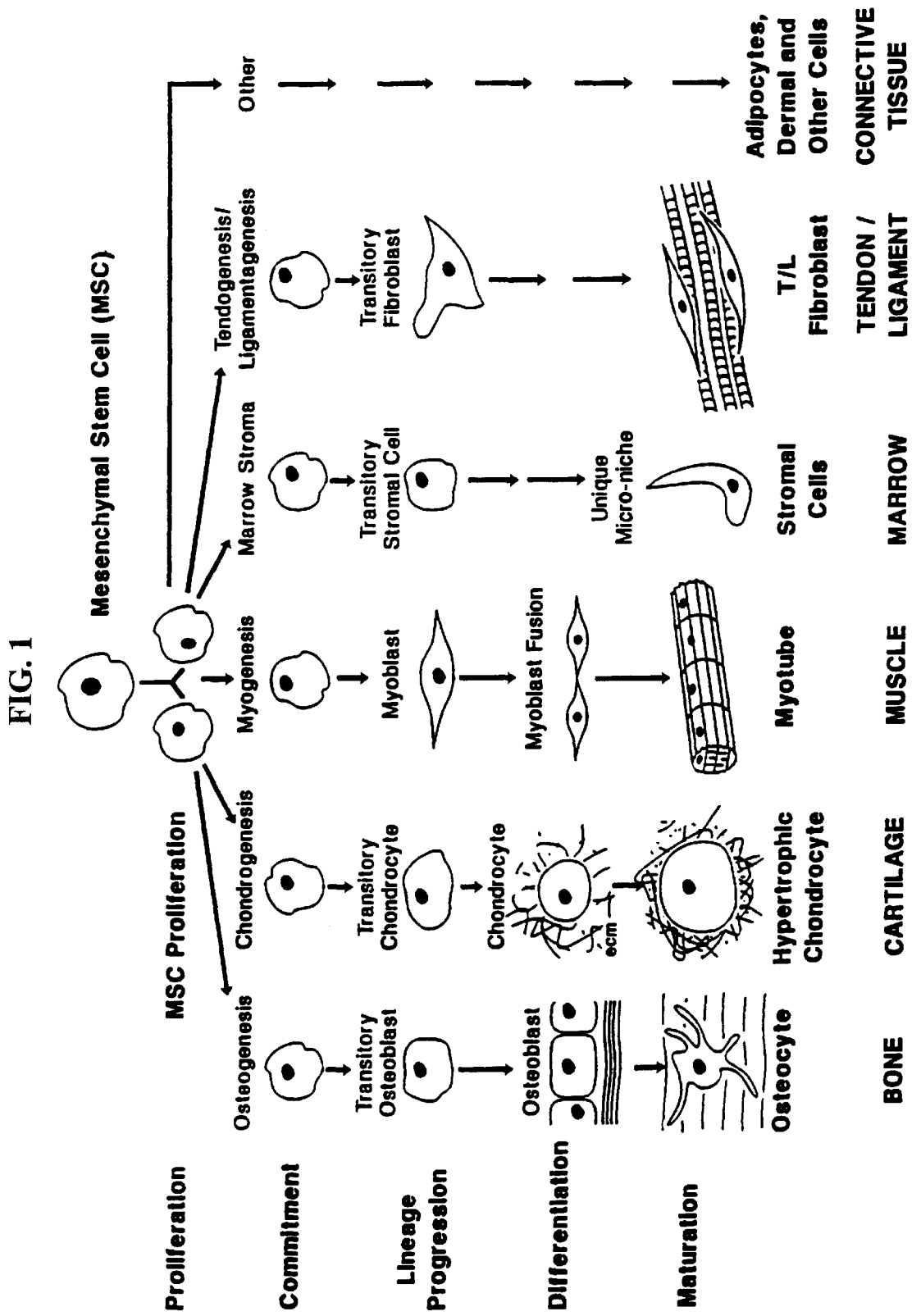

United States Patent [19]
Bruder et al.

[11] Patent Number: 5,942,225
[45] Date of Patent: Aug. 24, 1999

[54] LINEAGE-DIRECTED INDUCTION OF HUMAN MESENCHYMAL STEM CELL DIFFERENTIATION

[75] Inventors: Scott P. Bruder, Owings Mills, Md.; Arnold I. Caplan; Stephen E. Haynesworth, both of Cleveland Heights, Ohio

[73] Assignees: Case Western Reserve University, Cleveland, Ohio; Osiris Therapeutics, Inc., Baltimore, Md.

[21] Appl. No.: 08/899,414

[22] Filed: Jul. 23, 1997

Related U.S. Application Data

[62] Division of application No. 08/377,461, Jan. 24, 1995, Pat. No. 5,736,396.

[51] Int. Cl.$^6$ ........................................... C12N 5/00
[52] U.S. Cl. ........................... 424/93.7; 435/366; 435/372
[58] Field of Search ........................... 424/93.7; 435/366, 435/372

[56] References Cited

U.S. PATENT DOCUMENTS

| | | |
|---|---|---|
| 5,197,985 | 3/1993 | Caplan et al. . |
| 5,226,914 | 7/1993 | Caplan et al. . |
| 5,486,359 | 1/1996 | Caplan et al. . |
| 5,591,625 | 1/1997 | Gerson et al. . |
| 5,612,211 | 3/1997 | Wilson et al. . |
| 5,733,542 | 3/1998 | Haynesworth et al. . |
| 5,736,396 | 4/1998 | Bruder et al. . |

*Primary Examiner*—Leon B. Lankford, Jr.
*Attorney, Agent, or Firm*—Elliot M. Olstein; Raina Semionow

[57] ABSTRACT

Methods for in vitro or ex vivo lineage directed induction of isolated, culture expanded human mesenchymal stem cells comprising contacting the mesenchymal stem cells with a bioactive factor effective to induce differentiation thereof into a lineage of choice as well as such compositions including isolated culture expanded human mesenchymal stem cells and bioactive factors effective to induce directed lineage induction are disclosed. Further disclosed is this method which also includes introducing such culturally expanded lineage-induced mesenchymal stem cells into a host from which they have originated for purposes of mesenchymal tissue regeneration or repair.

36 Claims, 14 Drawing Sheets

FIG. 5

CHONDROGENIC LINEAGE

STEM CELL
↓
COMMITTED Chondroprogenitor : Type I Collagen
↓
Chondrogenic PROGENITOR : Type VI Collagen, CSPG-M
↓
Chondroblast : Type II Collagen, CDI(28Kd), CSPG-H (aggrecan)
↓
Chondrocyte I : 148Kd, link protein
↓
Chondrocyte II : 100 Kd, matrix vesicle production
↓
Hypertrophic Chondrocyte : Type X Collagen, 59Kd, 1,25-$(OH)_2$D,R
↓
Calcifying Chondrocyte : Type I Collagen, 63Kd, osteopontin, osteocalcin, osteonectin ns cells into a lineage of choice.
LINEAGE-DIRECTED INDUCTION OF HUMAN MESENCHYMAL STEM CELL DIFFERENTIATION This application is a divisional of U.S. application Ser. No. 08/377,461 filed Jan. 24, 1995, now U.S. Pat. No. 5,736,396.

The present invention provides methods for directing mesenchymal stem cells cultivated in vitro to differentiate into specific cell lineage pathways prior to, or at the time of, their implantation for the therapeutic treatment of pathologic conditions in humans and other species.

Mesenchymal stem cells (MSCs) are the formative pluripotent blast or embryonic-like cells found in bone marrow, blood, dermis, and periosteum that are capable of differentiating into specific types of mesenchymal or connective tissues including adipose, osseous, cartilaginous, elastic, muscular, and fibrous connective tissues. The specific differentiation pathway which these cells enter depends upon various influences from mechanical influences and/or endogenous bioactive factors, such as growth factors, cytokines, and/or local microenvironmental conditions established by host tissues. Although these cells are normally present at very low frequencies in bone marrow, a process for isolating, purifying, and mitotically expanding the population of these cells in tissue culture is reported in Caplan et al. U.S. Pat. Nos. 5,197,985 and 5,226,914.

In prenatal organisms, the differentiation of MSCs into specialized connective tissue cells is well established; for example embryonic chick, mouse or human limb bud mesenchymal cells differentiate into cartilage, bone and other connective tissues (1–5). In addition, a clonal rat fetus calvarial cell line has also been shown to differentiate into muscle, fat, cartilage, and bone (6). The existence of MSCs in post-natal organisms has not been widely studied with the objective of showing the differentiation of post-embryonic cells into several mesodermal phenotypes. The few studies which have been done involve the formation of bone and cartilage by bone marrow cells following their encasement in diffusion chambers and in vivo transplantation (7, 8). Recently, bone marrow-derived cells from young rabbits (800–1,000 g) have been shown to form adipocytic and osteogenic cells in vivo (9) and cloned bone marrow stromal cells of post-natal mice were shown to form adipocytes and osteogenic cells (10). Likewise, cells from chick periosteum have been isolated, expanded in culture, and, under high density conditions in vitro, shown to differentiate into cartilage and bone (11). Rat bone marrow-derived mesenchymal cells have been shown to have the capacity to differentiate into osteoblasts and chondrocytes when implanted in vivo (12, 6). Cells from various marrow sources of post-natal organisms have never been observed to exhibit myogenic properties, with multinuclear appearance being the most easily recognized characteristic in culture.

In a first aspect, the invention provides a method for effecting the lineage-directed induction of isolated, culture-expanded human mesenchymal stem cells which comprises contacting mesenchymal stem cells with a bioactive factor or combination of factors effective to induce differentiation thereof into a lineage of choice. More particularly, this method is one in which the bioactive factor induces differentiation of such cells into a mesenchymal lineage selected from the group consisting of osteogenic, chondrogenic, tendonogenic, ligamentogenic, myogenic, marrow stromagenic, adipogenic and dermogenic. Preferably, the cells are contacted ex vivo with one or more bioactive factors in this aspect, thereby providing a method free of any risks that may be associated with in vivo administration of any bioactive factors.

In another aspect, the method of the invention further provides administering to an individual in need thereof isolated culture-expanded human mesenchymal stem cells and a bioactive factor effective to induce differentiation of such cells into a lineage of choice. Preferably, the mesenchymal stem cells and bioactive factor are administered together or they may alternatively be administered separately. Particularly, this aspect of the method comprises administering the bioactive factor to an individual to whom a preparation comprising isolated autologous human mesenchymal stem cells has been, is being or will be administered.

In another aspect, the invention provides a method for inducing the in vivo production of human cytokines in an individual in need thereof which comprises administering to the individual isolated culture-expanded human mesenchymal stem cells and a bioactive factor effective to induce such cells to differentiate into a cytokine-producing mesenchymal lineage descendant in such individual. Preferably, the mesenchymal stem cells and bioactive factor are administered together or they may alternatively be administered separately.

In specific preferred examples of these aspects, the bioactive factor is a bone morphogenetic protein and the human MSCs are directed into the chondrogenic lineage; the bioactive factor is interleukin 1 and the human MSCs are directed into the stromal cell lineage (preferably the interleukin 1 is interleukin 1α); the bioactive factors are dexamethasone, ascorbic acid-2-phosphate and β-glycerophosphate and the human MSCs are directed into the osteogenic lineage; or the bioactive factor is selected from the group consisting of 5-azacytidine, 5-azadeoxycytidine and analogs of either of them and the human mesenchymal stem cells are directed into the myogenic lineage.

Another aspect of the invention provides a composition comprising isolated, culture-expanded human mesenchymal stem cells and a bioactive factor, or combination, effective to induce differentiation of such cells into a lineage of choice. Preferably the composition further comprises a tissue culture medium. Alternatively, the composition can comprise a medium suitable for administration to an animal particularly a human, in need thereof. This aspect of the invention also provides for specific embodiments using the bioactive factors identified above for lineage induction into the lineages associated therewith as described above.

FIG. 1 diagrammatically illustrates the mesengenic process by which mesenchymal stem cells differentiate into various lineage pathways.

Figure 2:
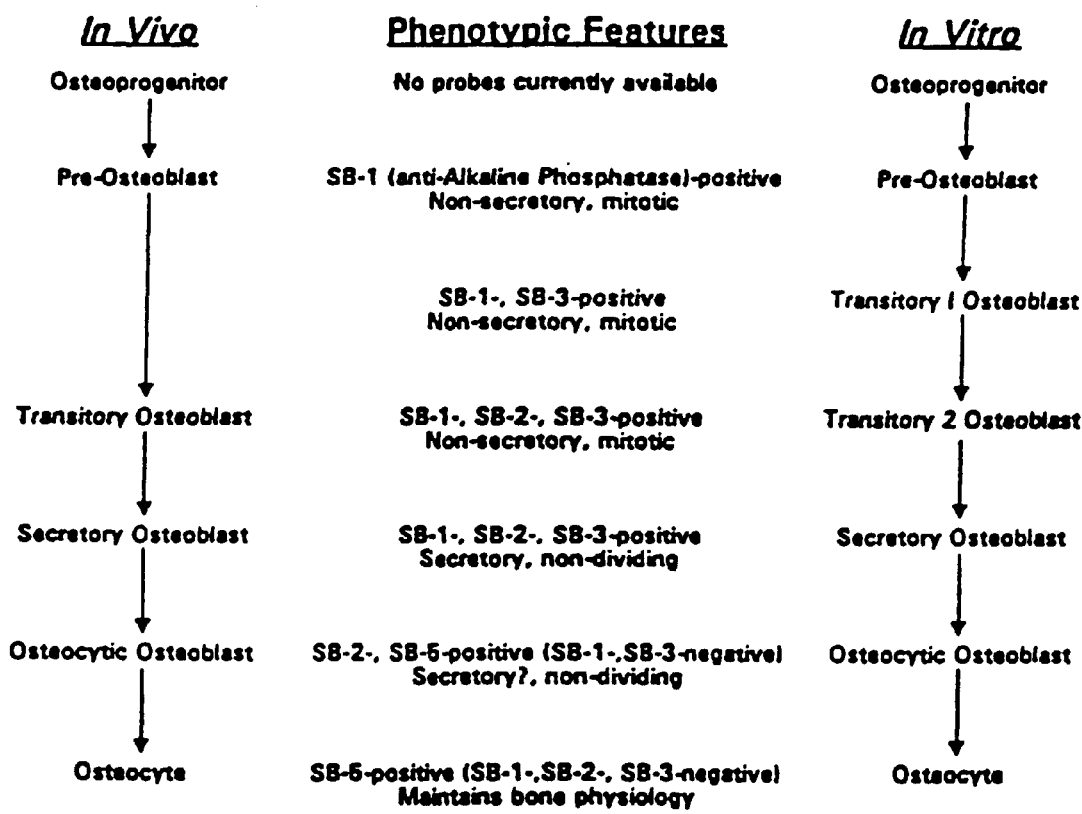

FIG. 2 diagrammatically illustrates the osteogenic differentiation pathway.

Figure 3:
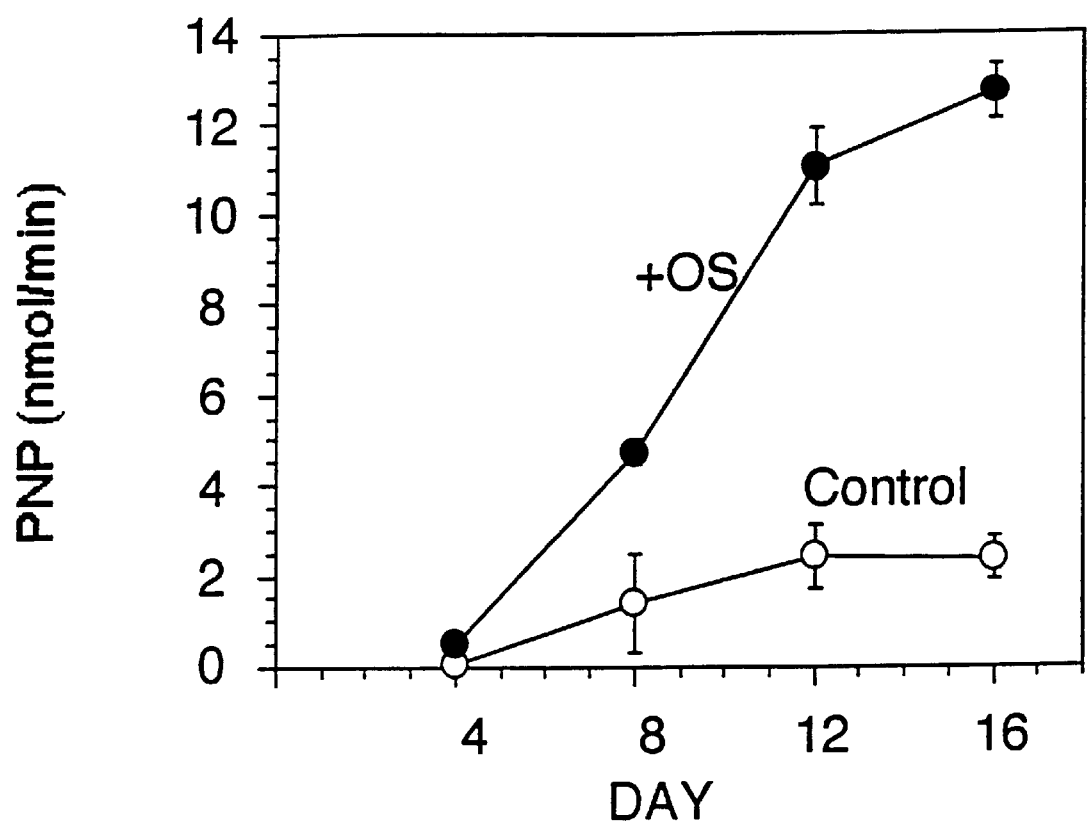

FIG. 3 graphically demonstrates the increase in alkaline phosphatase activity as a function of time in cultures, in the initial studies reported in Example 1.

Figure 4:
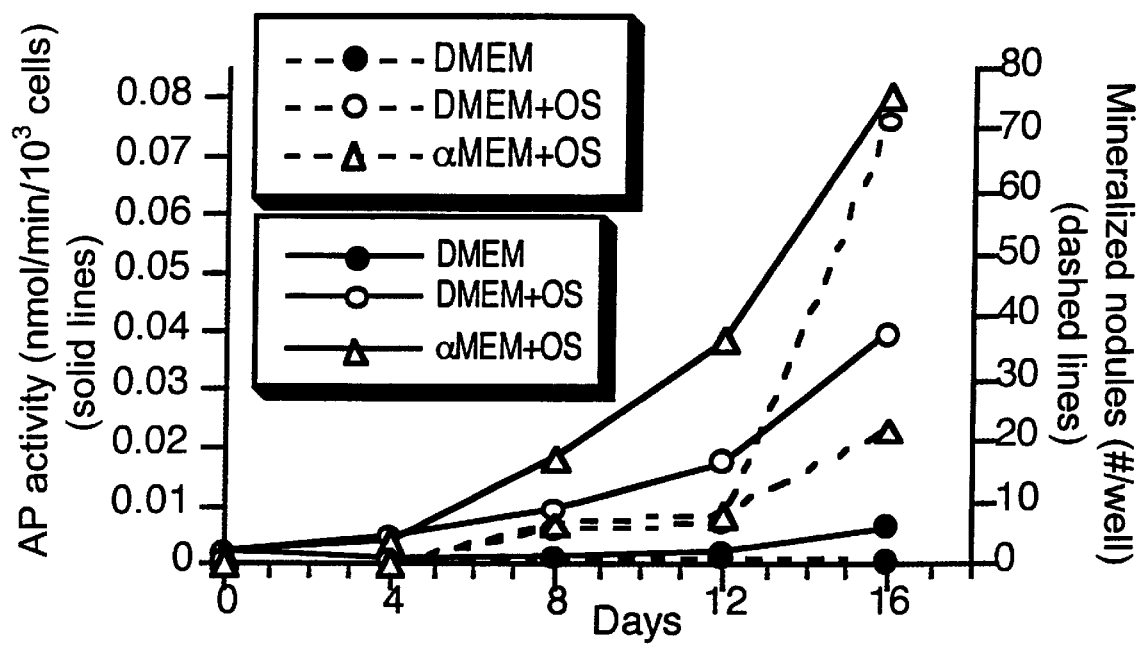

FIG. 4 shows results from the subsequent studies reported in Example 1.

FIG. 5 diagrammatically illustrates the chondrogenic differentiation pathway.

Figure 6:
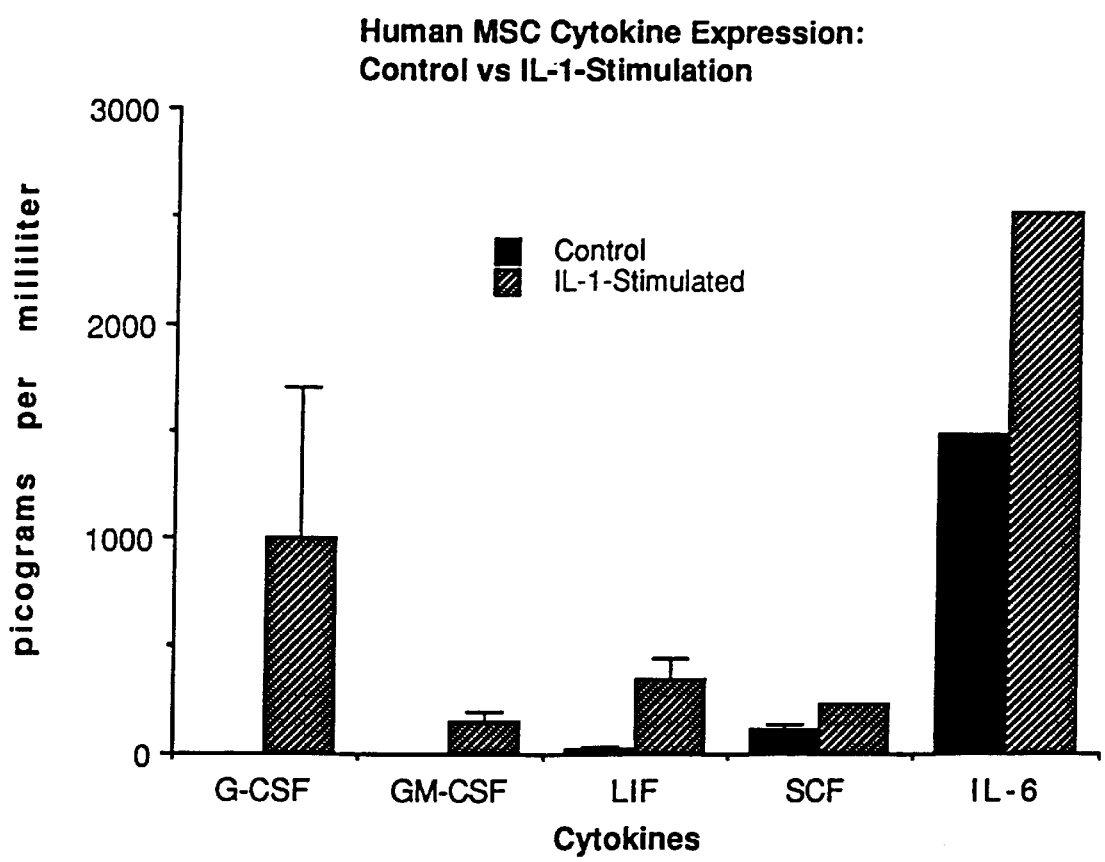

FIG. 6 shows the extent of human mesenchymal stem cell cytokine expression, with and without interleukin-1 stimulation, based on the experiments in Example 4.

Figure 7A:
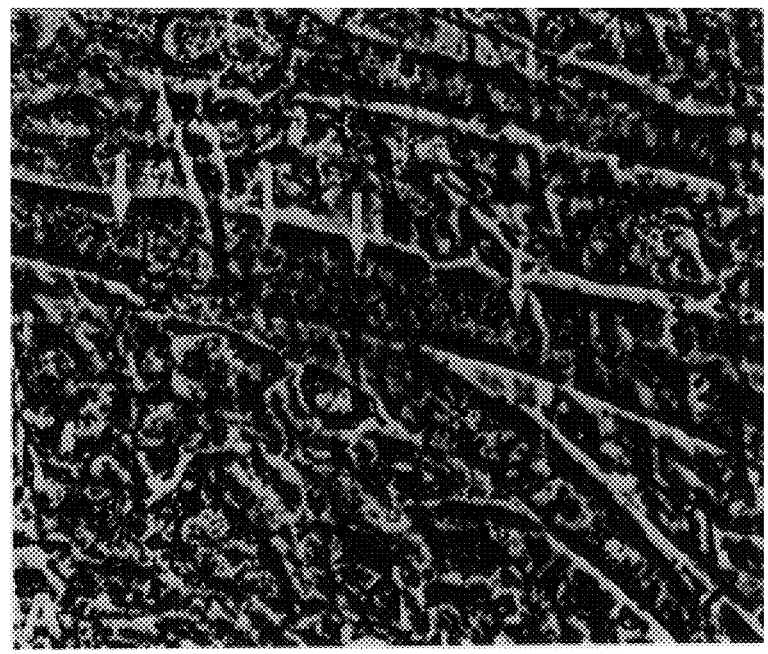
Figure 7B:
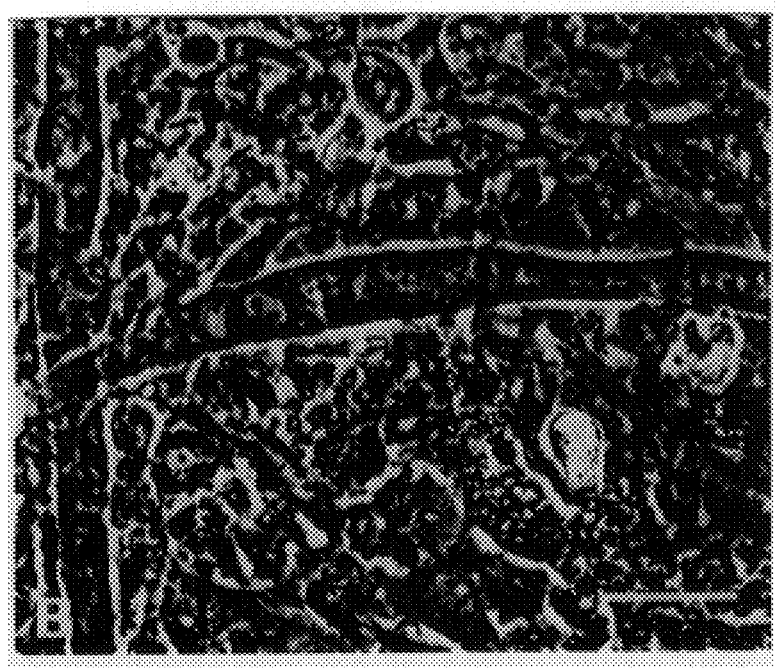

FIGS. 7A and 7B.

(A) Phase contrast micrograph of living culture of MSCs showing the multinucleated cells derived after exposure to 5-aza-CR. This micrograph shows a culture 2 weeks after treatment with 10 μM 5-aza-CR. Many nuclei (arrows) in the cell can be observed, but striations are not discernible.

(B) Phase contrast micrograph of living culture of normal rat fetal muscle cells prepared from the hindlimbs of 17-day-old rat fetuses. As with bone marrow MSC-derived myotubes, no discernible striations are apparent. Scale bar 50 μm.

Figure 8:
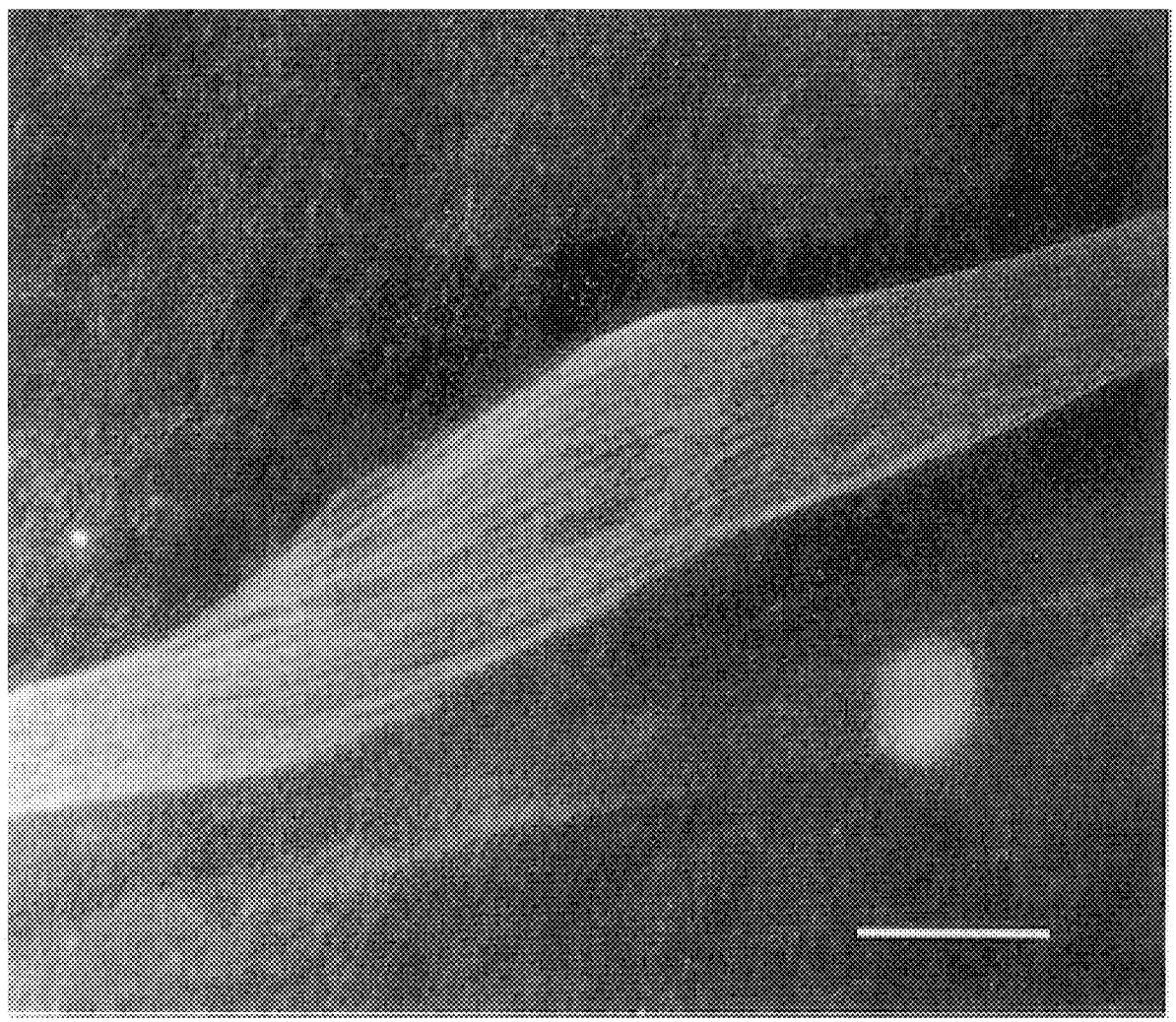

FIG. 8: Immunofluorescence staining for muscle-specific myosin in myotubes derived from rat bone marrow MSCs after exposure to 5-aza-CR. Myosin antibodies do not visualize cross striations, but the antibodies clearly illuminate longitudinal fibers. Scale bar 30 μm.

FIGS. 9A–9D: Myotubes derived from rat bone marrow MSCs 2 weeks [(A) and (B)] and 5 weeks [(C) and (D)] after exposure to 5-aza-CR. Phase contrast micrograph [(A) and (C)] and immunofluorescence staining for myosin [(B) and (D)]. (A) and (B), (C) and (D) are the same visual fields. Myotubes 2 weeks after 5-aza-CR exposure are stained with anti-myosin antibody, but those 5 weeks after exposure are not. Scale bar 50 μM.

Figure 10A:
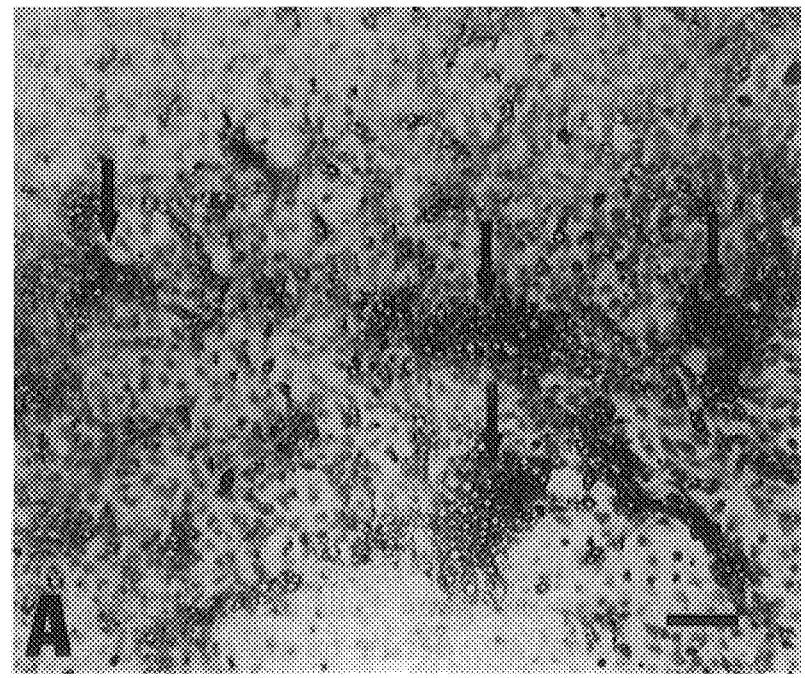
Figure 10B:
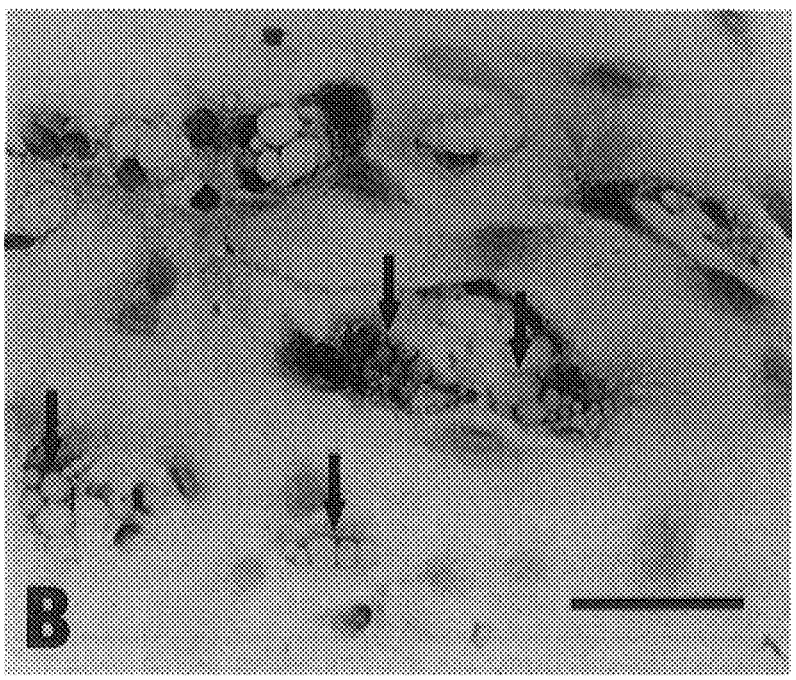

FIGS. 10A–10B: Micrograph of the 5-aza-CR-treated MSCs containing droplets in their cytoplasm; this culture was stained with Sudan Black. (A) Clusters of adipocytes (arrows) were observed; scale bar 200 μM. (B) Droplets are stained brown to black (arrows), which suggests that these droplets are lipid; scale bar 100 μM.

Figure 11:
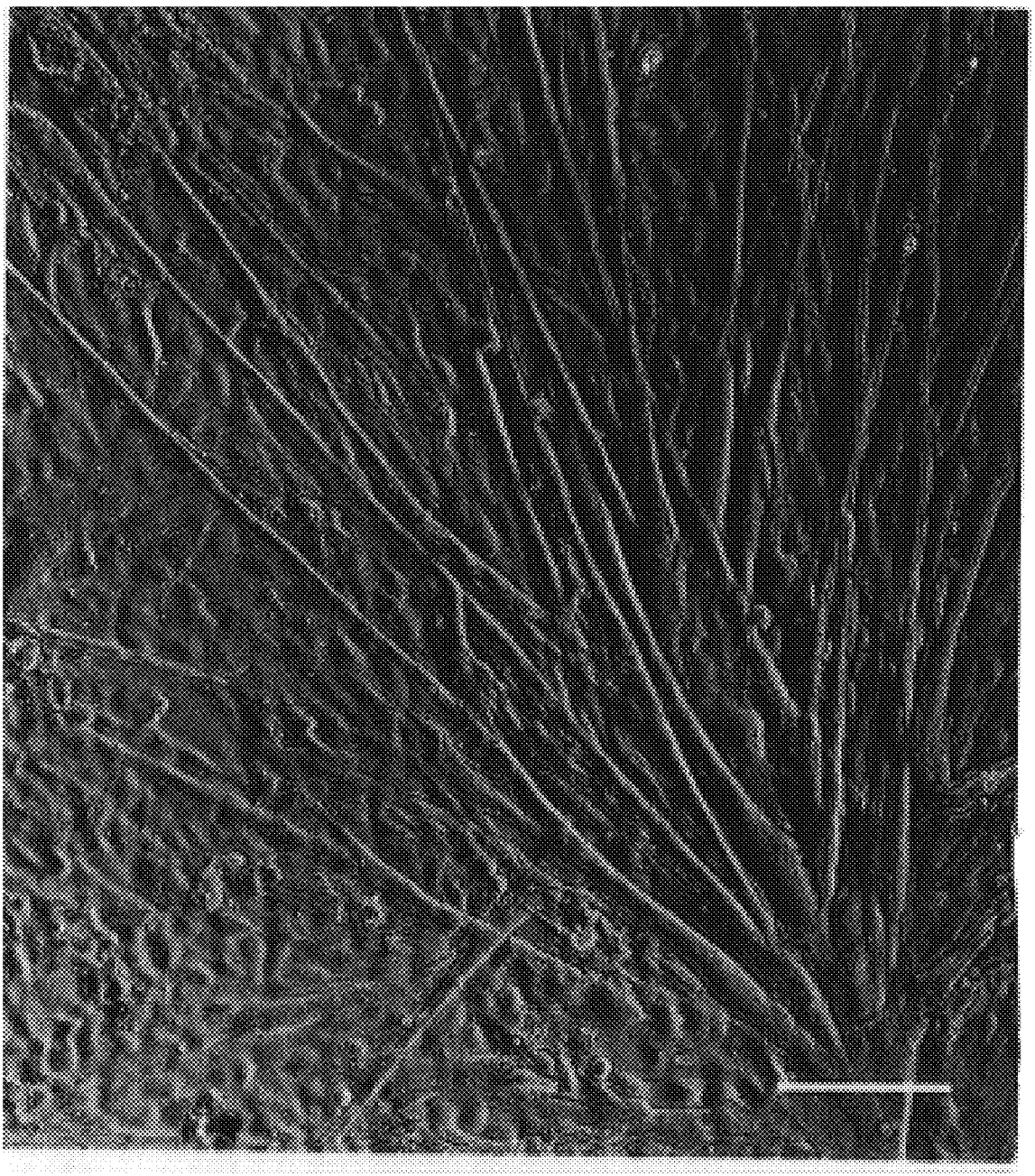
Figures 12A, 12B, 12C, 12D:
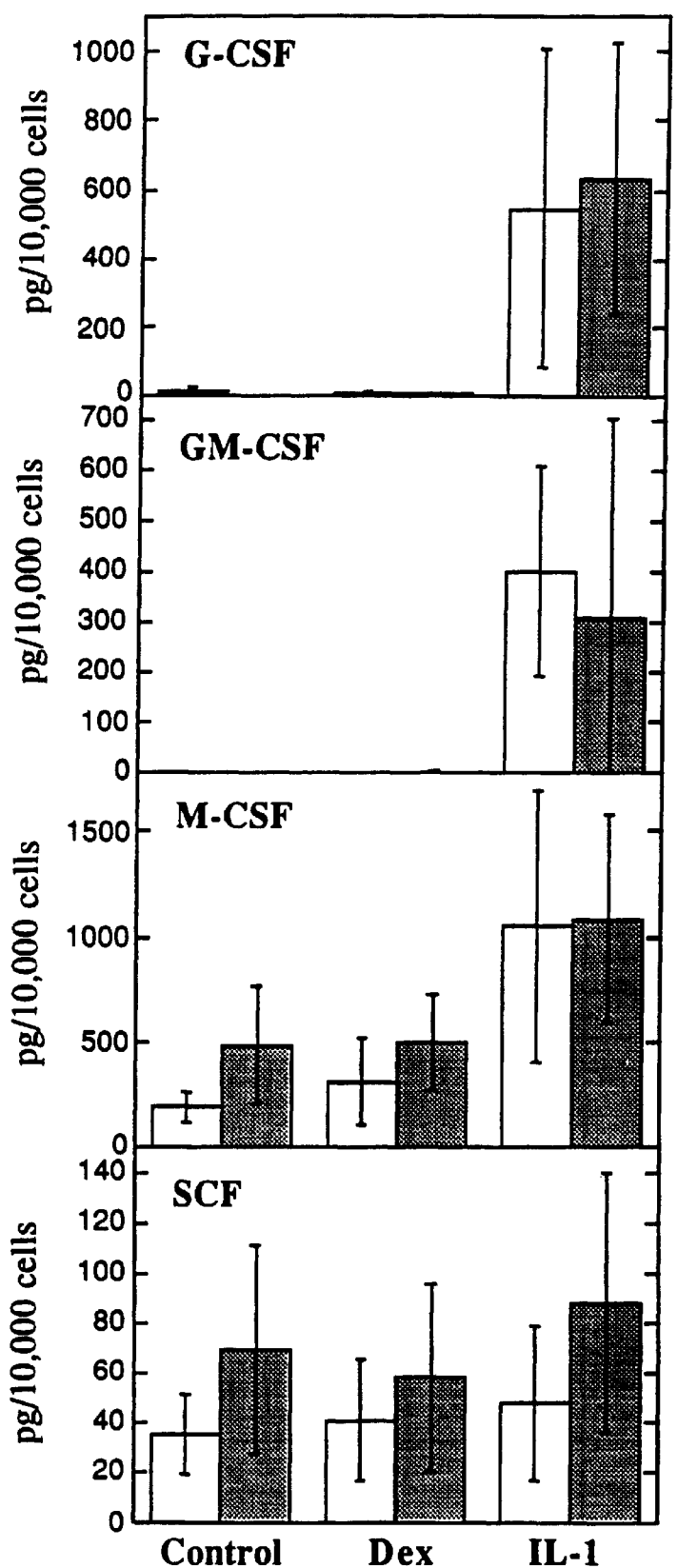

FIG. 11: Phase contrast micrograph of living culture of myogenic cells derived from rat bone marrow MSCs after exposure to 5-aza-CR. Following exposure to 5-aza-CR, these cells were cultured with 4 ng/ml bFGF for 10 days. Large myotubes can be seen; scale bar 300 μm.

FIGS. 12A–12D graphically illustrate the expression of G-CSF, GM-CSF, M-CSF and SCF, respectively, observed in the experiments reported by Example 6.

Figures 13A, 13B, 13C:
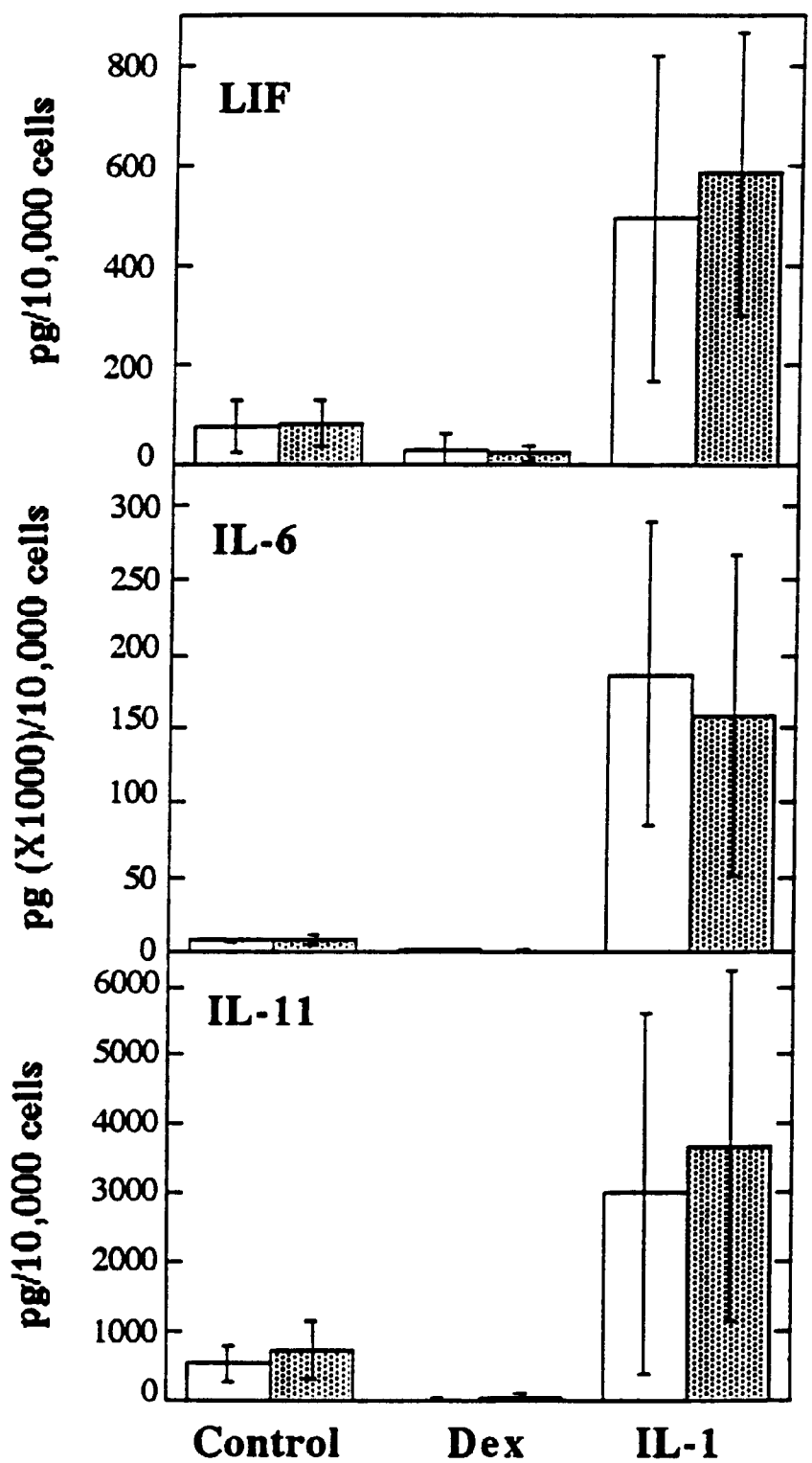

FIGS. 13A–13C graphically illustrate the expression of LIF, IL-6 and IL-11, respectively observed in the experiments reported by Example 6.

Figure 14:
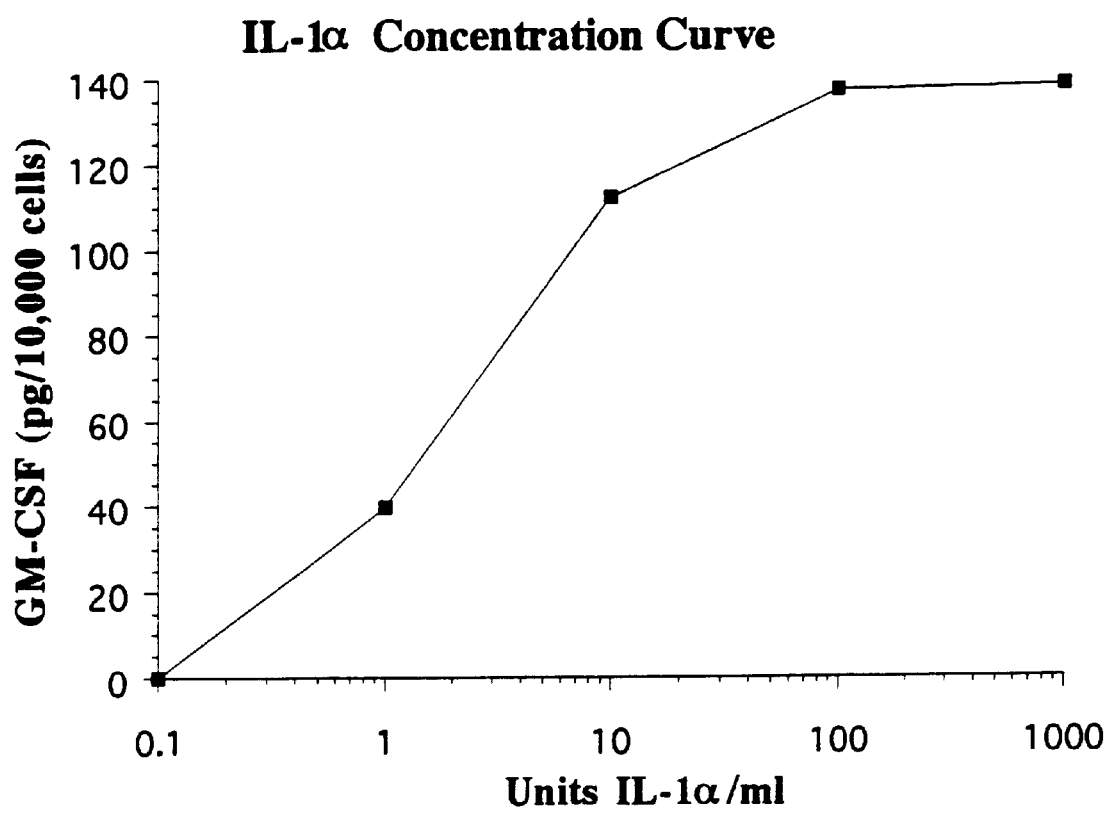

FIG. 14 graphically illustrates the dose dependent IL-1α induction of GM-CSF expression observed in the experiments reported by Example 6.

This invention has multiple uses and advantages. The first lies in the ability to direct and accelerate MSC differentiation prior to implantation back into autologous hosts. For example, MSCs which are directed in vitro to become osteogenic cells will synthesize bone matrix at an implant site more rapidly and uniformly than MSCs which must first be recruited into the lineage and then progress through the key differentiation steps. Such an ex vivo treatment also provides for uniform and controlled application of bioactive factors to purified MSCs, leading to uniform lineage commitment and differentiation. In vivo availability of endogenous bioactive factors cannot be as readily assured or controlled. A pretreatment step such as is disclosed herein circumvents this. In addition, by pretreating the MSCs prior to implantation, potentially harmful side effects associated with systemic or local administration of exogenous bioactive factors are avoided. Another use of this technique lies in the ability to direct tissue regeneration based on the stage of differentiation which the cells are in at the time of implantation. That is, with respect to bone and cartilage, the state of the cells at implantation may control the ultimate tissue type formed. Hypertrophic chondrocytes will mineralize their matrix and eventually pave the way for vascular invasion, which finally results in new bone formation. Clearly, MSCs implanted for the purpose of restoring normal hyaline cartilage must not progress down the entire lineage.

However, implants which are designed to repair articular surface defects and the underlying subchondral bone could benefit from a two-component system wherein the cells in the area of the future bone are directed ex vivo to become hypertrophic chondrocytes, while the cells in the area of the future articulating surface are directed only to become chondroblasts. In the area of stromal reconstitution, the ex vivo control of differentiation can optimize MSC cell populations for the elaboration of stage-specific cytokines requisite to the needs of the individual. Muscle morphogenesis can similarly be directed to create fast or slow twitch fibers, depending on the indication.

Isolation and Purification of Human Mesenchymal Stem Cells

The human mesenchymal stem cells isolated and purified as described here can be derived, for example, from bone marrow, blood, dermis or periosteum. When obtained from bone marrow this can be marrow from a number of different sources, including plugs of femoral head cancellous bone pieces, obtained from patients with degenerative joint disease during hip or knee replacement surgery, or from aspirated marrow obtained from normal donors and oncology patients who have marrow harvested for future bone marrow transplantation. The harvested marrow is then prepared for cell culture. The isolation process involves the use of a specially prepared medium that contains agents which allow for not only mesenchymal stem cell growth without differentiation, but also for the direct adherence of only the mesenchymal stem cells to the plastic or glass surface of the culture vessel. By creating a medium which allows for the selective attachment of the desired mesenchymal stem cells which were present in the mesenchymal tissue samples in very minute amounts, it then became possible to separate the mesenchymal stem cells from the other cells (i.e. red and white blood cells, other differentiated mesenchymal cells, etc.) present in the mesenchymal tissue of origin.

Bone marrow is the soft tissue occupying the medullary cavities of long bones, some haversian canals, and spaces between trabeculae of cancellous or spongy bone. Bone marrow is of two types: red, which is found in all bones in early life and in restricted locations in adulthood (i.e. in the spongy bone) and is concerned with the production of blood cells (i.e. hematopoiesis) and hemoglobin (thus, the red color); and yellow, which consists largely of fat cells (thus, the yellow color) and connective tissue.

As a whole, bone marrow is a complex tissue comprised of hematopoietic cells, including the hematopoietic stem cells, and red and white blood cells and their precursors; and a group of cells including mesenchymal stem cells, fibroblasts, reticulocytes, adipocytes, and endothelial cells which contribute to the connective tissue network called "stroma". Cells from the stroma regulate the differentiation of hematopoietic cells through direct interaction via cell surface proteins and the secretion of growth factors and are involved in the foundation and support of the bone structure. Studies using animal models have suggested that bone marrow contains "pre-stromal" cells which have the capacity to differentiate into cartilage, bone, and other connective tissue cells. (Beresford, J. N.: Osteogenic Stem Cells and the Stromal System of Bone and Marrow, Clin. Orthop., 240:270, 1989). Recent evidence indicates that these cells, called pluripotent stromal stem cells or mesenchymal stem cells, have the ability to generate into several different types of cell lines (i.e. osteocytes, chondrocytes, adipocytes, etc.) upon activation, depending upon the influence of a number of bioactive factors. However, the mesenchymal stem cells are present in the tissue in very minute amounts with a wide variety of other cells (i.e. erythrocytes, platelets, neutrophils, lymphocytes, monocytes, eosinophils, basophils, adipocytes, etc.).

As a result, a process has been developed for isolating and purifying human mesenchymal stem cells from tissue prior to differentiation and then culture expanding the mesenchymal stem cells to produce a valuable tool for musculoskeletal therapy. The objective of such manipulation is to greatly increase the number of mesenchymal stem cells and to utilize these cells to redirect and/or reinforce the body's normal reparative capacity. The mesenchymal stem cells are expanded to great numbers and applied to areas of connective tissue damage to enhance or stimulate in vivo growth for regeneration and/or repair, to improve implant adhesion to various prosthetic devices through subsequent activation and differentiation, or enhance hemopoietic cell production, etc.

Along these lines, various procedures are contemplated for transferring, immobilizing, and activating the culture-expanded, purified mesenchymal stem cells at the site for repair, implantation, etc., including injecting the cells at the site of a skeletal defect, incubating the cells with a prosthesis and implanting the prosthesis, etc. Thus, by isolating, purifying and greatly expanding the number of cells prior to differentiation and then actively controlling the differentiation process by virtue of their positioning at the site of tissue damage or by pretreating in vitro prior to their transplantation, the culture-expanded, mesenchymal stem cells can be utilized for various therapeutic purposes such as to alleviate cellular, molecular, and genetic disorders in a wide number of metabolic bone diseases, skeletal dysplasias, cartilage defects, ligament and tendon injuries and other musculoskeletal and connective tissue disorders.

Several media have been prepared which are particularly well suited to the desired selective attachment and are referred to herein as "complete Media" when supplemented with serum as described below. One such medium is an augmented version of Dulbecco's Modified Eagle's Medium-Low Glucose (DMEM-LG), which is well known and readily commercially available.

The commercial formulation is supplemented with 3700 mg/l of sodium bicarbonate and 10 ml/l of 100x antibiotic-antimycotic containing 10,000 units of penicillin (base), 10,000 $\mu$g of streptomycin (base) and 25 $\mu$g of amphotericin B/ml utilizing penicillin G (sodium salt), streptomycin sulfate, and amphotericin B as FUNGIZONE® in 0.85% saline.

The medium described above is made up and stored in 90 ml per 100 ml or 450 ml per 500 ml bottles at 4° C. until ready to use. For use, 10 ml or 50 ml of fetal bovine serum (from selected lots) is added to the bottles of media to give a final volume of 10% serum. The medium is warmed to 37° C. prior to use.

In this regard, it was also found that $BGJ_b$ medium (Gibco, Grand Island, N.Y.) with tested and selected lots of 10% fetal bovine serum (J. R. Scientific, Woodland, Cliaf., or other suppliers) was well suited for use in the invention. This medium, which was also a "Complete Medium", contained factors which also stimulated mesenchymal stem cell growth without differentiation and allowed for the selective attachment through specific protein binding sites, etc. of only the mesenchymal stem cells to the plastic surfaces of Petri dishes.

In addition, it was also found that the medium F-12 Nutrient Mixture (Ham) (Gibco, Grand Island, N.Y.) exhibited the desired properties for selective mesenchymal stem cell separation.

As indicated above, the complete medium can be utilized in a number of different isolation processes depending upon the specific type of initial harvesting processes used in order to prepare the harvested bone marrow for cell culture separation. In this regard, when plugs of cancellous bone marrow were utilized, the marrow was added to the complete medium and vortexed to form a dispersion which was then centrifuged to separate the marrow cells from bone pieces, etc. The marrow cells (consisting predominantly of red and white blood cells, and a very minute amount of mesenchymal stem cells, etc.) were then dissociated into single cells by sequentially passing the complete medium containing the marrow cells through syringes fitted with a series of 16, 18, and 20 gauge needles. It is believed that the advantage produced through the utilization of the mechanical separation process, as opposed to any enzymatic separation process, was that the mechanical process produced little cellular change while an enzymatic process could produce cellular damage particularly to the protein binding sites needed for culture adherence and selective separation, and/or to the protein sites needed for the production of monoclonal antibodies specific for said mesenchymal stem cells. The single cell suspension (which was made up of approximately $50-100 \times 10^6$ nucleated cells) was then subsequently plated in 100 mm dishes for the purpose of selectively separating and/or isolating the mesenchymal stem cells from the remaining cells found in the suspension.

When aspirated marrow was utilized as the source of the human mesenchymal stem cells, the marrow stem cells (which contained little or no bone chips but a great deal of blood) were added to the complete medium and fractionated with Percoll (Sigma, St. Louis, Mo.) gradients more particularly described below in Example 1. The Percoll gradients separated a large percentage of the red blood cells and the mononucleate hematopoietic cells from the low density platelet fraction which contained the marrow-derived mesenchymal stem cells. In this regard, the platelet fraction, which contained approximately $30-50 \times 10^6$ cells was made up of an undetermined amount of platelets, $30-50 \times 10^6$ nucleated cells, and only about 50–500 mesenchymal stem cells depending upon the age of the marrow donor. The low density platelet fraction was then plated in the Petri dish for selective separation based upon cell adherence.

In this regard, the marrow cells obtained from either the cancellous bone or iliac aspirate (i.e. the primary cultures) were grown in complete medium and allowed to adhere to the surface of the Petri dishes for one to seven days according to the conditions set forth in Example 1 below. Since minimal cell attachment was observed after the third day, three days was chosen as the standard length of time at which the non-adherent cells were removed from the cultures by replacing the original complete medium with fresh complete medium. Subsequent medium changes were performed every four days until the culture dishes became confluent which normally required 14–21 days. This represented a $10^3–10^4$ fold increase in the number of undifferentiated human mesenchymal stem cells.

The cells were then detached from the culture dishes utilizing a releasing agent such as trypsin with EDTA (ethylene diaminetetra-acetic acid) (0.25% trypsin, 1 mM EDTA (1x), Gibco, Grand Island, N.Y.). The releasing agent was then inactivated and the detached cultured undifferentiated mesenchymal stem cells were washed with complete medium for subsequent use.

The capacity of these undifferentiated cells to enter discrete lineage pathways is referred to as the mesengenic process, and is diagrammatically represented in FIG. 1. In the mesengenic process, MSCs are recruited to enter specific multi-step lineage pathways which eventually produce functionally differentiated tissues such as bone, cartilage, tendon, muscle, dermis, bone marrow stroma, and other mesenchymal connective tissues. For example, a detailed scheme for the differentiation pathway of bone forming cells is presented in FIG. 2. This lineage map implies the existence of individual controlling elements which recruit the MSCs into the osteogenic lineage, promote pre-osteoblast replication, and direct step-wise differentiation all the way to the terminal stage osteocyte. Substantial work has been reported that supports the view that each step of this complex pathway is controlled by different bioactive factors.

A similar lineage diagram has been developed for chondrocyte differentiation and is provided in FIG. 5. Again, progression of each lineage step is under the control of unique bioactive factors including, but not limited to, the family of bone morphogenetic proteins. Each modulator of the differentiation process, whether in bone, cartilage, muscle, or any other mesenchymal tissue, may affect the rate of lineage progression and/or may specifically affect individual steps along the pathway. That is, whether a cell is nascently committed to a specific lineage, is in a biosynthetically active state, or progresses to an end stage phenotype will depend on the variety and timing of bioactive factors in the local environment.

The bone and cartilage lineage potentials (i.e. osteochondrogenic potential) of fresh and expanded human mesenchymal stem cells were determined using two different in vivo assays in nude mice. One assay involved the subcutaneous implantation of porous calcium phosphate ceramics loaded with cultured mesenchymal stem cells; the other involved peritoneal implantation of diffusion chambers inoculated with cultured mesenchymal stem cells. Whole marrow and Percoll gradient separated aspirate fractions were also analyzed in these in vivo assays. Histological evaluation showed bone and cartilage formation in the ceramics implanted with the cultured mesenchymal stem cells derived from the femoral head and the iliac crest. Ceramics loaded with human mesenchymal stem cells at $5 \times 10^6$ cells/ml formed bone within the pores, while ceramics loaded with human mesenchymal stem cells at $10 \times 10^6$ cells/ml formed cartilage within the pores. While whole marrow has now been shown to form bone when placed as a composite graft with ceramics in a subcutaneous site in nude mice, the amount of bone produced is substantially less than that seen when culture expanded marrow-derived mesenchymal stem cells are used.

These results indicated that under certain conditions, culture expanded mesenchymal stem cells have the ability to differentiate into bone or cartilage when incubated as a graft in porous calcium phosphate ceramics. The environmental factors which influence the mesenchymal stem cells to differentiate into bone or cartilage cells appears, in part, to be the direct accessibility of the mesenchymal stem cells to growth and nutrient factors supplied by the vasculature in porous calcium phosphate ceramics; cells that are closely associated with vasculature differentiate into bone cells while cells that are isolated from vasculature differentiate into cartilage cells. The exclusion of vasculature from the pores of ceramics loaded with concentrated human mesenchymal stem cells prevented osteogenic differentiation and provided conditions permissive for chondrogenesis.

As a result, the isolated and culture expanded mesenchymal stem cells can be utilized under certain specific conditions and/or under the influence of certain factors, to differentiate and produce the desired cell phenotype needed for connective tissue repair or regeneration and/or for the implantation of various prosthetic devices. For example, using porous ceramic cubes filled with culture-expanded human mesenchymal stem cells, bone formation inside the pores of the ceramics has been generated after subcutaneous incubations in immunocompatible hosts. In a recent study (13), rat marrow in a composite graft with porous ceramic was used to fill a segmental defect in the femur of the rat. Bone was shown to fill the pores of the ceramic and anchor the ceramic-marrow graft to the host bone.

Factors which stimulate osteogenesis (i.e. are osteoinductive) from isolated human mesenchymal stem cells in accordance with the invention are present in several classes of molecules, including the following: bone morphogenic proteins, such as BMP-2 (14) and BMP-3 (15); growth factors, such as basic fibroblast growth factor (bFGF); glucocorticoids, such as dexamethasone (16); and prostaglandins, such as prostaglandin E1 (22). Further, ascorbic acid and its analogs, such as ascorbic acid-2-phosphate (17) and glycerol phosphates, such as β-glycerophosphate (18) are effective adjunct factors for advanced differentiation, although alone they do not induce osteogenic differentiation.

Factors which have chondroinductive activity on human MSCs are also present in several classes of molecules, including the following: compounds within the transforming growth factor-β (TGF-β) superfamily, such as (i) TGF-β1 (19), (ii) Inhibin A (20), (iii) chondrogenic stimulatory activity factor (CSA) (21) and (iv) bone morphogenic proteins, such as BMP-4 (22); collagenous extracellular matrix molecules, including type I collagen, particularly as a gel (23); and vitamin A analogs, such as retinoic acid (24).

Factors which have stromagenic inductive activity on human MSCs are also present in several classes of molecules, especially the interleukins, such as IL-1α (25) and IL-2 (26).

Factors which have myogenic inductive activity on human MSCs are also present in several classes of molecules, especially cytidine analogs, such as 5-azacytidine and 5-aza-2'-deoxycytidine.

The effect of these modulating factors on human MSCs is disclosed here for the first time. This is not represented to be an all-inclusive listing of potentially useful modulatory factors for inducing differentiation into a particular lineage, but illustrates the variety of compounds which have useful biologic activity for the purpose of promoting the step-wise progression of isolated human mesechymal stem cell differentiation.

EXAMPLE 1

Induced Osteogenic Differentiation of MSCs In Vitro

The objective of the experiments described in this example was to demonstrate that mesenchymal stem cells (MSCs) were directed along the osteogenic lineage pathway in vitro by providing appropriate bioactive factors in the tissue culture medium. This set of experiments illustrates just one example of how MSCs can be directed along the osteogenic lineage.

Initial Study

Human MSCs were harvested and isolated from bone marrow as described above. These cells were culture-expanded in DMEM-LG medium containing preselected 10% fetal bovine serum (Complete Medium). Fresh Complete Medium was replaced every 3–4 days until the cultures were near confluence, at which time the cells were liberated off the plates with trypsin, and reseeded onto new dishes at approximately 40% confluence (400,000 cells per 100 mm dish). These replated MSCs were allowed to attach overnight, after which the Complete Medium was replaced by a medium composed of DMEM-LG, 10% fetal bovine serum, and either 100 nM dexamethasone alone, or 100 nM dexamethasone with 50 $\mu$M ascorbic acid-2-phosphate, and 10 mM β-glycerophosphate (Osteogenic Supplement). The Osteogenic Supplement was replaced every 3 days. Cells were examined daily for morphologic changes. Selected plates were then analyzed for cell surface alkaline phosphatase (AP) activity, a marker for cells which have entered the osteogenic lineage. It is these cells which were subsequently responsible for synthesizing osteoid matrix. Standard enzyme histochemistry and biochemistry reagents were used to demonstrate activity of this cell surface protein. Additional specimens were evaluated for the presence of mineralized extracellular matrix nodules which correlate with the continued differentiation and phenotypic expression of a mature osteoblast population. Silver nitrate precipitation onto calcium phosphate crystals within the bone nodule was achieved through the standard Von Kossa staining technique.

The results indicate that after only three days of exposure to dexamethasone, MSCs in culture had already begun expressing alkaline phosphatase on their surface. By day six of culture, approximately 80% of the cells were AP positive. The gross organization of the culture dish had changed from near confluent whorls of fibroblast-like cells at day 1, to numerous areas of polygonal cells which were piled on top of each other. By day 9, many small nodules of birefringent extracellular matrix was associated with these foci of layered polygonal cells. These areas were positively stained by the Von Kossa method for mineral. Control cultures fed only Complete Medium never developed these mineralized bone nodules, and only rarely contained AP positive cells. By contrast, MSCs treated with Osteogenic Supplement uniformly acquired AP activity and synthesized mineralized extracellular matrix nodules throughout the dish. Although not osteoinductive themselves, the presence of ascorbic acid-2-phosphate and β-glycerophosphate in the complete Osteogenic Supplement further supports extracellular matrix maturation and mineral deposition, respectively. FIG. 3 graphically demonstrates the increase in alkaline phosphatase enzyme activity as a function of time in culture. By day 8 and beyond, substantially more enzyme activity is observed in cells exposed to Osteogenic Supplements (OS) than those cultured with control medium.

Taken together, these studies demonstrate that MSCs can be rapidly and uniformly stimulated to differentiate along the osteogenic lineage in vitro. Furthermore, not only are the MSCs recruited into the early steps within the lineage, evidenced by AP expression, but the MSCs progress through the lineage to become mature osteoblasts which secrete and mineralize a bone-like extracellular matrix. Further evidence for this comes from the observation that when chick MSCs are treated with Osteogenic Supplement, they progress through the stages of the osteogenic lineage depicted in FIG. 2 as determined by monoclonal antibody staining against stage-specific cell surface antigens.

Subsequent Study

Using published techniques, MSCs were purified from 3 different patients (ages 26–47), culture expanded (27), and seeded overnight onto 48-well culture plates at 20% confluence in DMEM-LG with 10% FBS from selected lots. Base media for comparison were DMEM-LG, BGJ$_b$, αMEM, and DMEM/F-12 (1:1). Triplicate cultures for each assay were grown in 10% FBS in the absence or presence of "Osteogenic Supplements" (OS) (100 nM dexamethasone, 50 $\mu$M ascorbic acid-2-phosphate, and 10 mM β-glycerophosphate (28). Media were changed every 3 days. Each set of cultures was assayed for cell number by the crystal violet assay, cell surface alkaline phosphatase (AP) by histochemistry and mineralized nodule formation by Von Kossa staining. AP enzyme activity was calculated by incubating live cultures with 5 mM p-nitrophenylphosphate in 50 mM Tris, 150 mM NaCl, pH 9.0 and quantifying the calorimetric reaction by scanning the samples at 405 nm on an ELISA plate reader. AP enzyme activity was expressed as nanomoles of product/minute/$10^3$ cells. The percentage of AP-positive cells in each well was determined from the stained cultures, and the number of mineralized nodules per well were counted. Assays were performed every 4 days for the 16 day culture period. The paired two-sample t-Test was performed on selected samples. The data in FIG. 4 represent one patient, although similar results were obtained from all specimens.

MSCs uniformly attached to the plates, assumed their characteristic spindle-shaped morphology, and proliferated to reach confluence within 8 days. During this period, and particularly beyond, the OS-treated cells developed a cuboidal morphology as their density increased, forming multiple layers. For clarity, only selected aspects of the parameters described above are graphically represented on FIG. 4. All specimens grown in BGJb+OS died within 3 days, while BGJb cultures survived for the duration of the protocol. For this reason, all BGJb data were omitted from the graphs. Highlights of the study demonstrate substantially greater proliferation in αMEM compared to DMEM/F-12 or DMEM alone (i.e., $p<0.01$ and $p<0.05$ at day 16). The addition of OS to αMEM cultures inhibited proliferation at days 8 and 12 ($p<0.04$ and $p<0.03$), but not by day 16 ($p>0.05$). αMEM+OS also stimulates a significant proportion of cells to express AP on their surface when compared to MSCs maintained in DMEM ($p<0.02$ at day 8. $p<0.01$ at day 16). However, no significant difference in the percent of AP cells is observed between αMEM with and without OS ($p>0.2$ at day 8, $p>0.05$ at day 16). Notably, αMEM+OS induces more AP activity than any other medium throughout the culture period, including αMEM or DMEM (i.e., $p<0.004$ and $p<0.002$ at day 16). However, there was no difference in AP activity between αMEM and DMEM+OS throughout the study period (i.e., $p>0.2$ at day 16). Of all media tested, the number of mineralized nodules by day 16 is greatest in DMEM+OS ($p<0.02$ compared to DMEM).

These investigations demonstrate that purified, culture-expanded human MSCs can be induced into the osteogenic lineage in vitro, thereby establishing a model for human osteoblast differentiation. Early in the culture period (day 8) only αMEM+OS induced substantial osteoblastic recruitment of MSCs (>50%), as noted by AP cell surface staining. By day 16, however, all cultures except DMEM contained >60% AP stained cells. In all media studied, addition of OS yields greater AP activity beyond 4 days. Although a large percentage of cells in most media were AP-stained at day 16, the substantial differences in the AP activity assay likely reflect the quantity of enzyme on the cell surface, and therefore, the degree of progression into the osteoblastic lineage. At the very least, OS are capable of up-regulating expression of this osteoblastic cell surface marker. Interestingly, despite less AP activity, DMEM+OS cells generated more mineralized nodules than αMEM+OS. This observation may suggest that within the 16 day culture period, DMEM+OS supports further osteogenic differentiation of MSCs than αMEM+OS. It is possible that, given more time, αMEM+OS would foster even more mineralized foci than DMEM+OS. Differences in the media favoring maintenance of the MSC phenotype (DMEM) evidenced by MSC-specific immunostaining, or maximal recruitment and induction into the osteogenic lineage (αMEM+OS), noted by the percent AP-positive cells and AP activity, are inherently interesting and warrant further examination. The use of various monoclonal and polyclonal antibodies against specific cell and matrix components during this inductive phenomenon are currently underway, and will provide further insight into the molecular nature of the in vitro differentiation process.

EXAMPLE 2

The Generation of Monoclonal Antibodies Against Human Osteogenic Cells Reveals Embryonic Bone Formation In Vivo And Differentiation of Purified Mesenchymal Stem Cells In Vitro It has been well-established that mesenchymal progenitor cells derived from bone marrow are capable of differentiating into osteoblasts. In addition, these mesenchymal stem cells (MSCs) also give rise to cartilage, tendon, ligament, muscle, and other tissues. However, knowledge of the steps involved in the commitment and differentiation of MSCs along these various lineages has been restricted, in part, by the lack of probes specific for cells at various stages within the osteogenic or other differentiation pathways. Since monoclonal antibodies are useful probes for studying differentiation, we immunized mice with intact living cell preparations of human bone marrow-derived MSCs induced into the osteogenic lineage in vitro. We screened hybridoma colonies against purified MSCs, MSCs undergoing osteogenic differentiation, and frozen sections of embryonic human limbs where long bones are developing around the cartilage rudiment. This screening protocol favors selection of antibodies which react with MSCs undergoing differentiation in vitro and human osteogenic cells in vivo. Using this approach, we have generated monoclonal antibodies against lineage stage-specific surface antigens on osteogenic cells derived from human marrow MSCs.

Using published techniques, MSCs were purified from 5 different patients (ages 28–46), culture expanded (29), and grown in DMEM-LG with 10% FBS and "Osteogenic Supplements" (100 nM dexamethasone, 50 μM ascorbic acid-2-phosphate, and 10 mm β-glycerophosphate (28). At days 3 and 6 of culture, early during alkaline phosphatase expression, and prior to mineralized nodule formation (30), the cells were liberated from the plates with 5 mM EGTA. Approximately 4 million 3 and 6 day cells were pooled for each of five weekly immunizations into Balbc/J mice. Using standard techniques, monoclonal hybridomas were produced, and culture supernatants were screened by a semiquantitative ELISA against purified MSCs, and MSCs cultured for 3 or 6 days with Osteogenic Supplements. Briefly, MSCs were plated on 96-well culture dishes, exposed to Osteogenic Supplements, and then reacted with culture supernatants followed by goat anti-mouse IgG conjugated to horseradish peroxidase. The secondary antibody was rinsed, and o-phenylenediamine substrate was added to the plates. Primary mouse monoclonal antibody binding was assessed by the olorimetric reaction quantified by scanning the wells at 490 nm on an ELISA plate reader. Colonies of interest were selected on the basis of differential binding to control MSCs and osteogenic cells derived from MSCS. Selected colonies were further screened by immunofluorescence on unfixed frozen sections of human embryonic limbs. Hybridoma colonies of interest were cloned and further immunocytochemical analyses were performed on a variety of normal and experimentally-derived tissues from human, rat, rabbit, chick, and bovine sources.

Nearly 10,000 hybridoma colonies were screened by the modified ELISA protocol described above. Based on differential binding to purified MSCs, or MSCs cultured for 3 and 6 days with Osteogenic Supplements, 224 colonies were selected for immunofluorescent screening against embryonic day 55–60 human limbs. The majority of those 224 colonies either reacted with multiple tissue types present in the developing limb, or were not detected in the developing bone. Thus far, 9 colonies have been identified which demonstrate specific immunoreactivity on cells of the osteogenic lineage. The patterns of reactivity vary; some hybridoma supernatants react with a large population of cells within the osteogenic collar and osteoprogenitor-containing periosteum, while others react with only those cells which appear to be actively involved in matrix synthesis. Two hybridoma colonies appear to react with osteogenic cells as well as hypertrophic chondrocytes. The results are summarized in Table 1.

TABLE 1

| Hybridoma Cell Line | Control MSCs | 3 day OS culture | 6 day OS culture |
| --- | --- | --- | --- |
| 20E8 | 0 | 1 | 8 |
| 13C9 | 0 | 1 | 3 |
| 5D9 | 0 | 1 | 2 |
| 18H4 | 0 | 3 | 5 |
| 18D4 | 0 | 2 | 4 |
| 10F1 | 0 | 0 | 2 |
| 13B12 | 0 | 4 | 2 |

Table 1 shows the immunoreactivity of selected hybridoma colonies against untreated MSCs, or MSCs cultured with Osteogenic Supplements (OS) for 3 or 6 days. Numbers reflect the relative amount of antibody bound in the ELISA assay described above.

These investigations indicate the presence of human osteogenic lineage stage-specific cell surface differentiation markers similar to those detailed for avian osteogenic cells (31). The staining of osteogenic cells in the developing limb supports the view that MSCs cultured with Osteogenic Supplements become "authentic" osteoblasts in culture. Osteogenic differentiation in vitro is thus confirmed by molecular probes which extend beyond traditional criteria of AP expression and mineralized nodule formation. Correlation of detailed in vitro observations with in vivo analyses of antigen expression will be useful in further studies of osteogenesis. Characterization of the specific tissue culture elements, i.e., bioactive factors, which promote progression of cells through the osteogenic lineage steps will be crucial. Identification of osteogenic cell surface, and/or extracellular matrix antigens should provide further insight into bone cell physiology. These and other monoclonal antibodies currently under investigation will prove useful in future studies of MSC differentiation.

EXAMPLE 3

Induced Chondrogenic Differentiation of MSCs In Vitro

The objective of the experimentation described in this example was to demonstrate that mesenchymal stem cells (MSCs) were directed along the chondrogenic lineage pathway in vitro by providing appropriate bioactive factors in the tissue culture medium. This set of experiments represents just one example of how MSCs can be directed along the chondrogenic lineage. Human MSCs were harvested and isolated from bone marrow as described above. Cells were culture-expanded in DMEM-LG medium containing preselected 10% fetal bovine serum (Complete Medium). Fresh medium was replaced every 3–4 days until the cultures were near confluence, at which time the cells were liberated off the plates with trypsin, and reseeded onto new dishes at approximately 50% confluence (500,000 cells per 100 mm dish). These replated MSCs were allowed to attach overnight, after which the Complete Medium was replaced by DMEM-LG with 10% fetal bovine serum, and 5 mg/ml partially purified Bone Morphogenic Protein (Chondrogenic Supplement), supplied by Dr. Marshall R. Urist. This Chondrogenic Supplement was replaced every 3 days. Cells were examined daily for morphologic changes. Selected plates were then analyzed immunohistochemically for CSPG-M, a marker for cells which have entered the chondrogenic lineage. It is these cells which were then actuated for synthesizing the Type II collagen matrix of cartilage. Standard immunohistochemistry reagents were used to demonstrate the presence of this extracellular matrix protein. Additional specimens were evaluated for the presence of Toluidine Blue-stained nodules which correlated them with the continued differentiation and phenotypic expression of a mature chondrocyte population. Von Kossa staining for the presence of mineralized nodules of hypertrophic chondrocytes was negative.

The results indicated that after only three days of exposure to the Chondrogenic Supplement, MSCs in culture had already begun expressing CSPG-M into their extracellular matrix. The gross organization of the culture dish had changed from whorls of fibroblast-like cells at day 1, to numerous foci of multi-layered round or polygonal cells surrounded by a thin layer of fibroblastic cells resembling a perichondrium. The extracellular matrix of these nodules was strongly immunoreactive for Type II collagen. Control cultures fed only Complete Medium never developed these cartilage nodules. Taken together, these studies demonstrate that MSCs have been stimulated to differentiate along the chondrogenic lineage in vitro. Furthermore, not only were the MSCs recruited into the early steps within the lineage, evidenced by CSPG-M expression, but the MSCs progressed along the lineage to become mature chondrocytes which secreted Type II collagen-rich extracellular matrix. Thus far, terminal differentiation of chondrocytes derived from MSCs, evidenced by hypertrophic cells in a calcified matrix, has not been observed in vitro. This finding reflects the need for designing a Chondrogenic Supplement specifically aimed at promoting this terminal differentiation step. Interestingly, Pacifici and his collaborators (32) have devised a medium containing retinoic acid which stimulates terminal differentiation of chick chondrocytes in vitro.

The additive to Complete Medium which constitutes Chondrogenic Supplement in the example above is only one of the factors known to stimulate chondrogenic cell differentiation or proliferation in vitro.

EXAMPLE 4

Induced Marrow Stromal Cell Differentiation of MSCs in Vitro

The purpose of the experimentation described in this example was to demonstrate that human marrow-derived MSCs were directed along the stromagenic lineage pathway in vitro by providing appropriate bioactive factors in the culture medium. Human marrow-derived MSCs were isolated from bone marrow and expanded in culture as described above. In order to demonstrate the ability of human MSCs to be induced along the marrow stromal cell lineage, specific cytokine expression was measured as a marker of differentiation. MSCs were grown under conditions which favor MSC proliferation without differentiation using medium consisting of DMEM-LG containing preselected 10% fetal bovine serum (Complete Medium), or conditions which favor expression and differentiation into the marrow stromal phenotype using medium comprising Complete Medium plus 10 U/ml Interleukin-1α (IL-1α) (Stromagenic Supplement (SS)). Conditioned culture media from these tissue culture populations were analyzed for the presence of cytokines using commercial sandwich ELISA bioassays (R&D Systems).

The cytokines that were assayed are those that are known to be secreted by stromal cells and which influence hematopoiesis. These include interleukin-3 (IL-3), interleukin-6 (IL-6), granulocyte colony stimulating factor (G-CSF), granulocyte-macrophage colony stimulating factor (GM-CSF), stem cell factor (SCF), leukemia inhibitory factor (LIF) and transforming growth factor-beta-2 (TGF-β2). In each case, second passage MSCs were plated onto 35 mm culture plates at a density of approximately 30% confluence (30,000 cells per 35-mm plate). After allowing overnight attachment of the cells, the culture media were removed, and replaced with either Complete Medium or Complete Medium plus Stromagenic Supplement. FIG. 6 illustrates the cytokine expression of human MSCs under the two plating conditions. In the absence of IL-1α, MSCs expressed G-CSF, GM-CSF, LIF and SCF at very low levels, but express IL-6 in high abundance. In comparison, after 3 days of IL-1-α stimulation, dramatically higher levels of cytokines were detected for all of the above species. MSCs did not express IL-3 or TGF-β2 under either of the two culture conditions. These data show that IL-I-α enhances MSC expression of a cytokine profile that has been documented to support differentiation of the hematopoietic stem cell and which is characteristic of differentiated marrow stromal cells.

EXAMPLE 5

Induced Myogenic Differentiation of MSCs In Vitro

The purpose of the study described in this example was to demonstrate that 5-azacytidine induces mesenchymal stem cells (MSCs) to differentiate along the myogenic lineage.

The compound, 5-azacytidine (5-aza-CR; Sigma Chemical Co., St. Louis, Mo.), an analogue of cytidine, causes hypomethylation of some cytosine in DNA which may be involved in activating phenotype-specific genes. The mouse embryonic cell lines, C3H/10T1/2 C18 and Swiss 3T3, after exposure to 5-aza-CR, have been shown to be converted into 3 different mesodermal cell lineages, myoblast, adipocyte and chondrocyte (33-34). In part, it appears that the mechanism by which 5-aza-CR activates myogenic genes involves MyoD1 (35-36). With the above in mind, we have exposed rat bone marrow-derived MSCs to 5-aza-CR and have focused our analysis on their conversion to myogenic phenotypes.

Femora and tibiae of male Fisher rats (Charles River, Indianapolis, Ind.) with an average body weight of 100 g were collected and the adherent soft tissues were removed.

Several isolates of marrow cells were from 250 g rats. Meticulous dissection of the long bones to remove soft tissue was done to insure that myogenic precursors were not carried into the marrow preparation. In this regard, myogenic cells were never observed in untreated MSC cultures. Both ends of the bones were cut away from the diaphyses with bone scissors. The bone marrow plugs were hydrostatically expelled from the bones by insertion of 18-gauge needles fastened to 10 ml syringes filled with Complete Medium consisting of DMEM containing selected lots of 10% fetal calf serum (FCS; IR Scientific Inc., Woodland, Calif.), 5% horse serum (HS; Hazleton Biologics Inc., Lenexa, Kans.), and antibiotics (Gibco Laboratories; penicillin G, 100 U/ml; streptomycin, 100 µg/ml; amphotericin B, 0.25 µg/ml). The needles were inserted into the distal ends of femora and proximal ends of tibias and the marrow plugs expelled from the opposite ends. The marrow plugs were disaggregated by sequential passage through 18-gauge, 20-gauge, and 22-gauge needles and these dispersed cells were centrifuged and resuspended twice in Complete Medium. After the cells were counted in a hemocytometer, $5 \times 10^7$ cells in 7–10 ml of complete medium were introduced into 100 mm petri dishes. Three days later, the medium was changed and the non-adherent cells discarded. Medium was completely replaced every 3 days. Approximately 10 days after seeding, the dishes became nearly confluent and the adherent cells were released from the dishes with 0.25% trypsin in 1 mM sodium EDTA (Gibco Laboratories, Grand Island, N.Y.), split 1:3, and seeded onto fresh plates. After these once passaged cells became nearly confluent, they were harvested and used for the experiments described below. We refer to these cells as rat marrow-derived MSCs. In total, 8 separate rat marrow-derived MSC preparations were used in this study. The cells were routinely cultured in Complete Medium at 37° C. in a humidified atmosphere of 5% $CO_2$.

The twice passaged MSCs were seeded into 35-mm dishes at three cell densities, 500, 5,000, and 50,000 cells/dish. Beginning 24 hr after seeding, these cultures were treated for 24 hr with Myogenic Medium consisting of complete medium containing various concentrations of 5-aza-CR. After the cultures were washed twice with Tyrode's balanced salt solution (Sigma Chemical Co.), the medium was changed to complete medium without added 5-aza-CR and subsequently changed twice a week until the experiment was terminated, 40 days after the treatment. As described in detail in the results, various culture conditions were tested to attempt to optimize the 5-aza-CR effects, especially to optimize myogenesis.

Twice passaged rat bone marrow MSCs were seeded into 35-mm dishes at 5,000 cells/dish and treated with four concentrations (0.1 µM, 0.3 µM, 1 µM and 10 µM) of 5-aza-2'-deoxycytidine (5-aza-dCR; Sigma Chemical Co.) in the same way as described above for 5-aza-CR. At various times during treatment, the morphology of the cultures was observed.

The living cultures were examined every day with a phase-contrast microscope (Olympus Optical Co., Ltd., Tokyo, Japan), and eventually some of the cultures were fixed for histology or immunohistochemistry. Muscle cells were first identified morphologically in phase contrast by the presence of multinucleated myotubes, and subsequently immunohistochemically by the presence of the skeletal muscle-specific protein, myosin. Contraction of the putative muscle cells was stimulated by a drop of 1 mM acetylcholine (Sigma Chemical Co.) in Tyrode's. For immunohistochemistry, cultured cells were fixed with −20° C. methanol (Fisher Scientific Co., Fair Lawn, N.J.) for 10 min and incubated with a mouse monoclonal antibody to rat fast twitch skeletal myosin (Sigma Chemical Co.; ascites fluid, 1/400 dilution) in PBS (phosphate buffered saline, pH7.4) containing 0.1% BSA (bovine serum albumin; Sigma Chemical Co.). The second antibody was biotin-conjugated sheep anti-mouse IgG (Organon Teknika Corp., West Chester, Pa.; 1/50 dilution) followed by treatment with Texas red-conjugated avidin (Organon Teknika Corp.; 1/4, 000 dilution). All incubations were for 30 min at room temperature, each preceded by blocking for 5 min with PBS containing 1% BSA, followed by two 5-min washes in PBS. The cells were mounted in Fluoromount-G (Fisher Biotech, Pittsburgh, Pa.) and observed with an Olympus microscope (BH-2) equipped for fluorescence and photographed with Kodak TMAX 400 film.

Second passage rat bone marrow MSCs were plated into 96-well plates at limiting dilution of one cell/well; cells were plated in medium consisting of 50% Complete Medium and 50% conditioned medium, which was obtained from rat bone marrow cells near confluence cultured in Complete Medium for 2 days. From a total of 384 wells, 50 colonies were detected; these were subcultured, maintained, and eventually 4 survived. These 4 clones were treated with 5-aza-CR as mentioned above and scored for myogenic or adipocytic morphologies.

First passage rat bone marrow cells were exposed to 10 µM 5-aza-CR for 24 hr and plated into 96-well plates at limiting dilution of one cell/well as above. The number of clones exhibiting adipocyte (Sudan Black positive) or myogenic, multinucleated cell morphologies was determined.

To compare the conversion capacity of bone marrow MSCs to various mesodermal phenotypes with that of pure fibroblasts, we exposed rat brain fibroblasts to either 5-aza-CR or 5-aza-CdR. Whole cerebra of brains of three male Fisher rats were collected from the inside of the skulls and cut into small pieces with a sharp scalpel. These pieces were transferred to a 50-ml conical centrifuge tube, centrifuged at 500×g for 10 min, resuspended in 10 ml of Tyrode's balanced salt solution, and homogenized with a loose-fitting Dounce homogenizer. The homogenate was incubated with 0.1% collagenase (CLS2, 247 U/mg; Worthington Biochemical Co., Freehold, N.J.) at 37° C. for 3 hr, during which time it was vortexed for 30 sec every 30 min. After treatment, the released cells were passed through a 110-µm Nitex filter, centrifuged, resuspended in 10 ml of low glucose DMEM-LG (Gibco Laboratories) containing 10% FCS, and cultured in three 100-mm culture dishes at 37° C. in a $CO_2$ incubator. The medium was changed twice a week and cells were cultured until the dishes reached confluence.

Third passage rat brain fibroblasts were seeded into 35-mm dishes at a density of 50,000 cells/dish and treated with 1 µM, 3 µM or 10 µM 5-aza-CR or 0.1 µM, 0.3 µM or 1 µM 5-aza-CdR in the same way as rat marrow MSCs. After 24 hr, the medium was changed to DMEM-LG containing 10% FCS, 5% HS and 50 nM hydrocortisone without added 5-aza-CR or 5-aza-CdR and subsequently changed twice a week until the experiment was terminated.

Myogenic cells derived from rat bone marrow MSCs were compared with normal fetal rat myogenic cells, since a substantial data base exists for the latter. Muscle cells were dissociated from the hindlimb muscles of 17-day-old Fisher rat fetuses with 0.2% trypsin (Sigma Chemical Co.) in calcium- and magnesium-free Tyrode's for 35 min at 37° C. with occasional agitation. After they were passed through a 110-μm Nitex filter, the concentration of fibroblasts was reduced by incubating cell suspensions for 30 min in Falcon plastic dishes, which results in preferential attachment of the fibroblasts. A suspension of $5 \times 10^5$ single cells that did not attach to the uncoated dish was plated in a collagen-coated (1.5 ml of 0.14% gelatin, J. T. Baker Chemical Co., Phillipsberg, N.J.) 35-mm plastic culture dish containing 2 ml of 79% DMEM, 10% FCS, 10% HS and 1% non-essential amino acids (Gibco Laboratories). Cells were grown at 37° C. in a humidified atmosphere of 5% $CO_2$.

Cultures of rat bone marrow-derived MSCs (5,000 cells/ 35 mm dish) were exposed to various concentrations of 5-aza-CR (0, 1, 3, 10, 20, and 50 μM) 24 hr after seeding the cells into culture dishes. The medium containing the 5-aza-CR was removed after the 24-hr exposure period and replaced with medium lacking 5-aza-CR. Seven days after this exposure, long multinucleated cells were observed in some of the dishes treated with more than 3 μM 5-aza-CR (FIG. 7A); the cells in these cultures were approximately 80% of confluence. The number of such multinucleated cells increased as isolated colonies or groupings, and reached a maximum (9 colonies in 10 of 35-mm dishes) 2 weeks after the initial treatment. The number of such cells decreased (6 colonies in 10 of 35-mm dishes) by 5 weeks after treatment; 7 disappeared probably due to their contraction and detachment from the dishes and 4 new colonies appeared during this time period; a substantial proportion of the multinucleated cells remained for up to 40 days after the initial exposure, which was the longest observational period. The morphology of the multinucleated cells, observed by phase contrast microscopy of living cultures (FIG. 7A), was similar to that of rat muscle in culture. We observed no discernible striations, as are routinely observed in embryonic chick myogenic cells in culture, although myotubes derived from myogenic cells obtained from normal fetal rat limbs also did not show striations (FIG. 7B). Thus, neither the myotubes derived from MSCs nor those obtained from normal rat embryos exhibit striations under the conditions employed in these studies. Waves of spontaneous contractions or twitching of some of these multinucleated cells was observed when viewing the living cultures. The contraction of these cells could also be stimulated by placing a drop of an acetylcholine solution onto these cells, which is a further indication that these cells are myogenic.

Figure 9A:
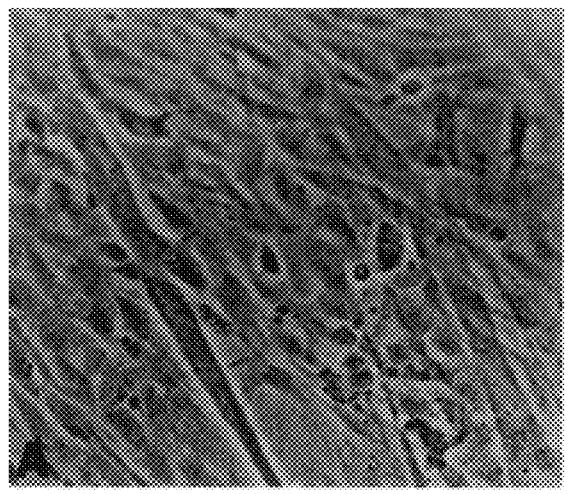
Figure 9B:
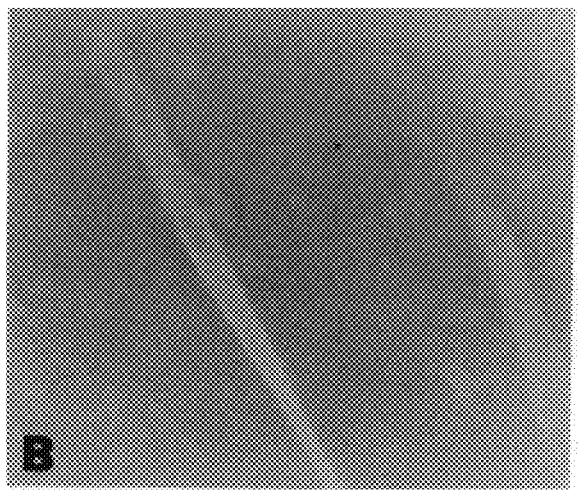
Figure 9C:
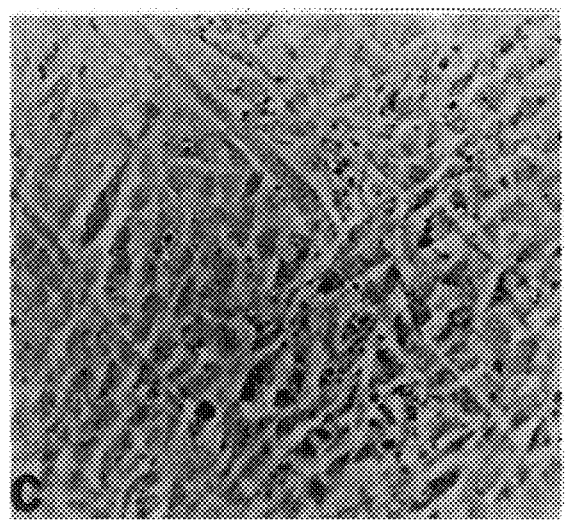
Figure 9D:
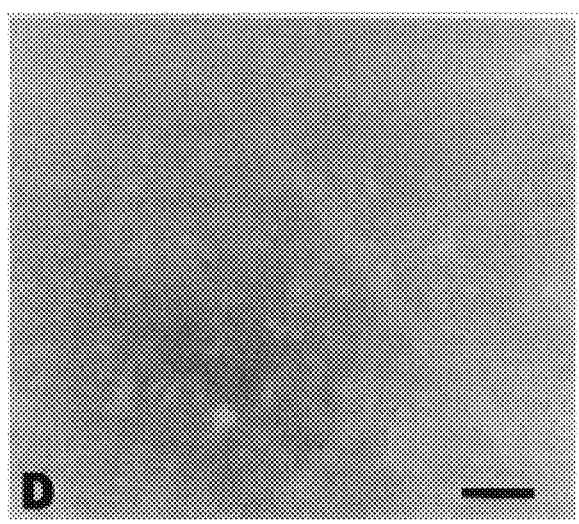

To further confirm the identity of these multinucleated cells, antibody to skeletal muscle specific myosin was presented to a fixed preparation of these cultures. FIG. 8 shows a myotube stained positively with the anti-myosin antibody; again, cross striations could not be observed. We also stained myotubes 2 weeks and 5 weeks after 5-aza-CR treatment with anti-myosin antibody. Myotubes 2 weeks after treatment were stained strongly positive (FIG. 9A and 9B), although those 5 weeks after treatment were stained weakly (FIG. 9C and 9D).

The effect of 5-aza-CR appeared to be dependent on the concentration presented to MSCs. No myotubes were found in dishes treated with 0 or 1 μM 5-aza-CR, but in those treated with 3–50 μM 5-aza-CR, myotubes were observed with comparable incidence (Table 2).

TABLE 2

Number of Groupings of Myotubes or Adipocytes Found Per Culture for MSCs Exposed to Different Concentrations of 5-aza-CR

| [5-aza-CR] Conc. | Myotubes | Adipocytes | SI* |
|---|---|---|---|
| 0 μM | 0/12 | 3/12 | 27% |
| 1 μM | 0/12 | 19/12 | 21% |
| 3 μM | 3/12 | 16/12 | 15% |
| 10 μM | 4/9 | 19/9 | 12% |
| 20 μM | 2/5 | 9/5 | 7% |
| 50 μM | 2/5 | 8/5 | 6% |

Secondary cultures of rat bone marrow cells were plated at 5,000 cells per 35 mm dish, treated with the indicated concentration of 5-aza-CR, and observed 14 days after treatment. The numbers for the incidence of myotubes and adipocytes indicate the total number of phenotypically discernible groupings observed and the total number of culture dishes examined.

To measure Survival Index (SI*) in the presence of 5-aza-CR, MSCs were seeded at 200 cells/35 mm dish and treated with 5-aza-CR 24 hr after plating. After 14 days, colonies containing more than 10 cells were counted, and this number was multiplied by 100% and divided by 200 to generate the percentage.

When cells were treated with higher concentrations of 5-aza-CR, the number of cells on the plate decreased, with 10 μM appearing to be the most effective concentration with regard to the maximum number of myogenic cells and cell survival (plating efficiency of Table 2). Thus, all subsequent experiments were done with 10 mM 5-aza-CR.

To examine the effect of 5-aza-2'-deoxycytidine (5-aza-dCR), a deoxy analogue of 5-aza-CR, rat bone marrow MSCs were treated with 0.3 μM, 1 μM, and 10 μM 5-aza-dCR in the same way as 5-aza-CR. Of the concentrations tested, 0.3 μM 5-aza-CdR gave the highest incidence of myogenic conversion, and the observed incidence was much higher than for cells exposed to 10 μM 5-aza-CR (Table 3).

TABLE 3

Number of Groupings of Myotubes Found Per Culture for MSCs Exposed to Different Concentrations of 5-aza-CdR and 5-aza-CR

| Cytidine Analog | Conc. | Myotubes | SI* |
|---|---|---|---|
| 5-aza-CdR | 0.1 μM | 10/10 | 16% |
| 5-aza-CdR | 0.3 μM | 24/10 | 10% |
| 5-aza-CdR | 1.0 μM | 3/10 | 3% |
| 5-aza-CdR | 10 μM | 1/10 | 1% |
| 5-aza-CR | 10 μM | 7/10 | 14% |

*Survival Index

Secondary cultures of rat bone marrow cells were plated at 5,000 cells per 35 mm dish, treated with the indicated concentration of 5-aza-dCR or 5-aza-CR, and observed 14 days after treatment. The numbers for the incidence of myotubes indicate the total number of phenotypically discernible groupings observed and the total number of culture dishes examined.

To measure Survival Index in the presence of 5-aza-CdR or 5-aza-CR, MSCs were seeded at 200 cells/35 mm dish and treated with 5-aza-dCR or 5-aza-CR 24 hr after plating. After 14 days, colonies containing more than 10 cells were counted, and this number was multiplied by 100% and divided by 200 to generate the percentage.

To eliminate the possibility of contamination by surrounding muscle-derived myoblasts at the time of bone marrow harvesting, second passage rat bone marrow MSCs were cloned as described herein. Four clones of indistinguishable morphologies were obtained from this procedure and were exposed to 5-aza-CR for 24 hr; for emphasis, no cells in these clones exhibited muscle-like characteristics or positive immunostaining for muscle specific myosin prior to exposure to 5-aza-CR. Of 4 clones exposed to 5-aza-CR, one clone exhibited the distinctive morphology of myotubes and adipocytes, which we interpret to indicate that non-muscle cells were converted to or influenced to become myoblasts or adipocytes.

First passage rat bone marrow-derived MSCs were exposed to 10 $\mu$M 5-aza-CR for 24 hr and cloned. From a total of 768 wells, 136 colonies were detected. Of these 136 colonies, 7 (5%) exhibited a myogenic phenotype, 27 (20%) exhibited an adipocytic phenotype, and the other colonies lacked morphologies obviously related to discernible phenotypes.

To test the effect of 5-aza-CR and 5-aza-dCR on non-MSC preparations, we exposed brain fibroblasts to these same reagents. Rat brain fibroblasts were seeded into 35-mm dishes at a density of 50,000 cells/dish and treated with 1 $\mu$M, 3 $\mu$M or 10 $\mu$M 5-aza-CR or 0.1 $\mu$M, 0.3 $\mu$M or 1 $\mu$M 5-aza-dCR in the same way as for rat MSCs. Each group had 9 dishes and cells were surveyed until 14 days after exposure. At day 7, all dishes reached confluence, except for the group treated with 10 $\mu$M 5-aza-CR. No fat cells nor myotubes could be found in any dishes during the period of observation.

MSCs were collected from the bone marrow of young (4 week-old, 100 g) and adult (3 month-old, 250 g) donor rats and passaged, and the number of colonies of myogenic phenotype after exposure to 5-aza-CR were compared (Table 4).

TABLE 4

Number of Groupings of Myotubes Per Culture of MSCs Exposed to 5-aza-CR

| FCS | HS | HC | Myotubes |
| --- | --- | --- | --- |
| 10% | 5% | + | 11/5 |
| 10% | 5% | – | 8/5 |
| 10% | 0% | + | 2/5 |
| 10% | 0% | – | 0/5 |
| 5% | 0% | + | 0/5 |
| 5% | 0% | – | 0/5 |
| 0% | 5% | + | 0/5 |
| 0% | 5% | – | 0/5 |

Secondary cultures of rat bone marrow MSCs were plated at 5,000 cells per 35 mm dish, treated with $\mu$M 5-aza-CR and 24 hr later changed to DMEM with different levels of FCS, HS, or 50 $\mu$M HC, and observed 14 days after exposure to 5-aza-CR was terminated. The numbers for the incidence of myotubes indicate the total number of culture dishes examined.

MSCs from young donor rats had more myogenic colonies than those from adult rats. Second passage cultures of young donor MSCs exposed to 5-aza-CR produced more myogenic colonies compared with MSCs from older donors tested in cultures from the first to fourth passage.

A variety of culture conditions were tested to attempt to optimize the expression of the myogenic phenotype of cultured MSCs exposed to 5-aza-CR. Exposed cells were cultured in medium containing various concentrations of FCS, HS, basic fibroblast growth factor (bFGF) and hydrocortisone. Table 4 shows that medium containing 10% FCS, 5% HS and hydrocortisone appeared to be the optimal medium for MSC expression of myogenic properties. Medium containing bFGF seemed to increase the expression of the myogenic phenotype (Table 5), although this may be related to an increase in the number of myoblasts due to myoblast division as opposed to increased conversion from progenitor cells.

TABLE 5

Comparison of 5-aza-CR-Induced Myotubes by Young and Old Rat Bone Marrow MSCs With Each Passage

| | Initial Cell Number | | First | Second | Third | Fourth |
| --- | --- | --- | --- | --- | --- | --- |
| Young (100g) | 50,000/dish | +bFGF | 3/5 | 9/5 | 3/5 | 0/5 |
| | 50,000/dish | –bFGF | 3/5 | 16/15 | 2/5 | 1/5 |
| | 5,000/dish | +bFGF | 1/5 | 10/5 | 2/5 | 2/5 |
| | 5,000/dish | –bFGF | 3/5 | 13/15 | 2/5 | 5/5 |
| Old (250g) | 50,000/dish | +bFGF | 1/5 | 0/5 | 2/5 | 0/5 |
| | 50,000/dish | –bFGF | 0/5 | 0/5 | 0/5 | 0/5 |
| | 5,000/dish | +bFGF | 1/5 | 0/5 | 1/5 | 3/5 |
| | 5,000/dish | –bFGF | 0/5 | 0/5 | 0/5 | 2/5 |

Cells were cultured in DMEM with 10% FCS, 5% HS and 50 $\mu$M HC, with or without bFGF. The numbers for the incidence of myotubes indicate the total number of phenotypically discernible colonies or groupings observed and the total number of culture dishes examined. MSCs were obtained from young (100 g) or old (250 g) rats.

In addition, bone marrow-derived MSCs were plated at 500 cells/dish, 5,000 cells/dish, and 50,000 cells/dish and then exposed to 5-aza-CR. At 500 cells/dish, myogenic cells were first observed at 20 days after treatment, with the cells becoming confluent 25 days after treatment; 2 clusters of myogenic cells were observed in 5 dishes 29 days after treatment. At 5,000 cells/dish, myogenic cells were first observed at 7 days, with the cells becoming confluent 10 days after treatment; 3 clusters were observed in 4 dishes 14 days after treatment. At 50,000 cells/dish, myogenic cells were observed at 6 days, with the cells becoming confluent at 7 days after treatment; 10 clusters were observed in 5 dishes 14 days after treatment.

The observations presented here indicate that rat bone marrow MSCs have the capacity to differentiate into the myogenic lineage in vitro following a brief exposure to 5-aza-CR. The observed myogenic cells exhibited the characteristic multinucleated morphology of myotubes, contracted spontaneously, contracted when exposed to acetylcholine, and stained positively with a monoclonal antibody to skeletal muscle-specific myosin, although these myotubes never exhibited apparent striations. However, normal rat myoblasts collected from fetal rat muscle did not, in our hands, form obviously striated myotubes in culture. We have attempted to exclude the possibility of contamination by committed myogenic cells by meticulously removing attached soft tissue from the bones at the time of bone marrow harvesting. Importantly, we have never observed myotubes in any culture of rat bone marrow MSCs in hundreds of preparations, except for those exposed to sufficient concentrations of 5-aza-CR. In addition, a clone of rat bone marrow MSCs was converted to both myogenic and adipocytic phenotypes after treatment with 5-aza-CR, which we interpret to mean that non-muscle progenitor cells were converted into these two phenotypes. Since skeletal muscle has not been observed in bone marrow, we believe that 5-aza-CR converts these marrow-derived MSCs into the myogenic cells.

EXAMPLE 6

Cytokine Expression by Human Mesenchymal Stem Cells In Vitro: Effects of IL-1α and Dexamethasone The objective of the present study was to further establish the phenotypic characteristics of cultured MSCs through identification of a cytokine expression profile. We used commercial ELISAs to identify and measure the levels of expression of cytokines that are known to be important in the regulation of cell division, differentiation or expression of a variety of mesenchymal phenotypes. We identified MSC cytokine expression under culture conditions that we have previously reported allow MSCs to mitotically expand without differentiation (constitutive culture-expansion medium). In addition, we assayed cytokine expression by MSCs in culture medium supplemented with dexamethasone or IL-1α. Dexamethasone has been reported to induce the differentiation of osteo-progenitors into osteoblasts. In contrast, IL-1α, which is secreted into the marrow microenvironment by a variety of cells during the inflammatory response, has been reported to enhance the bone marrow stroma's capacity to support hematopoiesis and thus may play a role in controlling the differentiation and/or expression of bone marrow stromal fibroblasts.

The data from these analyses show that cultured MSCs express a unique cytokine profile. In addition, dexamethasone and IL-1α alter the MSC cytokine expression profile in different ways. These data add to our understanding of the unique phenotypic profile of MSCs, and also identify macromolecules whose expression is developmentally regulated as MSCs differentiate or modulate thier phenotype towards the osteogenic lineage or marrow stromal phenotype.

MATERIALS AND METHODS

MSC Isolation and Culture-Expansion

Bone marrow was obtained from six human donors, 3 male and 3 female of diverse ages (Table 6).

TABLE 6

Donor Characteristics

| Donor # | Donor Age | Clin. Cond. | Gender |
|---|---|---|---|
| 1 | 39 | NHL* | F |
| 2 | 58 | breast cancer | F |
| 3 | 38 | myelodysplasia | F |
| 4 | 3 | medulloblastoma | M |
| 5 | 28 | Hodgkin's Lymphoma | M |
| 6 | 47 | AML* | M |

*NHL = non-Hodgkin's lymphoma; AML = acute myelogenous leukemia

Each donor was in remission from cancer and was undering marrow harvested for future autologous bone marrow transplantation. Approximately 10 ml of unfractionated bone marrow was obtained from the harvest and used in the assays in this study. MSCs were purified and cultured by a modification of previously reported methods. Briefly, bone marrow aspirates were transferred from their syringes into 50 ml conical tubes containing 25 ml of complete medium consisting of Dulbecco's Modified Eagles Medium supplemented with fetal bovine serum (FBS) from selected lots, to a final volume of 10%. The tubes were spun in a Beckman table top centrifuge at 1200 rpm in a GS-6 swing bucket rotor for 5 mi to pellet the cells. The layer of fat that forms at the top of the samples and the supernatants were aspirated using a serological pipet and discarded. The cell pellets were resuspended to a volume of 5 ml with Complete Medium and then transferred to the top of preformed gradients of 70% Percoll. The samples were loaded into a Sorvall GS-34 fixed angle rotor and centrifuged in a Sorvall High Speed Centrifuge at 460×g for 15 min. The low density fraction of approximately 15 ml (pooled density=1.03 g/ml) was collected from each gradient and transferred to 50 ml conical tubes to which were added 30 ml Complete Medium. The tubes were centrifuged at 1200 rpm to pellet the cells. The supernatants were discarded and the cells were resuspended in 20 ml of Complete Medium and counted with a hemocytometer after lysing red blood cells with 4% acetic acid. Cells were adjusted to a concentrated of $5 \times 10^7$ cells per 7 ml and seeded onto 100-mm culture plates at 7 ml per plate.

Culture and Passage of MSCs

MSCs were cultured in Complete Medium at 37° C. in a humidified atmosphere containing 95% air and 5% $CO_2$, with medium changes every 3–4 days. When primary culture dishes became near confluent, the cells were detached with 0.25% trypsin containing 1 mM EDTA (GIBCO) for 5 min at 37° C. The enzymatic activity of trypsin was stopped by adding ½ volume of FBS. The cells were counted, split 1:3, and replated in 7 ml of Complete Medium. These first passage cells were allowed to divide for 4–6 days until they became near confluent. Near-confluent first passage cells were trypsinized and replated into the assay formats as described below.

Quantitative ELISA

Levels of cytokine expression by MSCs were measured using quantitative ELISA. ELISA kits (R&D Systems, Minneapolis Minn.) with antibody specificities for the following cytokines were purchased; interleukin-3 (IL-3), interleukin-6 (IL-6), interleukin-11 (IL-11), granulocyte colony stimulating factor (G-CSF), granulocyte-macrophage colony stimulating factor (GM-CSF), macrophage colony stimulating activity (M-CSF), stem cell factor (SCF), leukemia inhibitory factor (LIF) and transforming growth factor-beta-2 (TGF-β2). Near-confluent, first passaged MSCs were replated into 35-mm plates at 50,000 cells per plate and allowed to attach overnight. Culture conditions were then changed to one of three test conditions: fresh Complete Medium; Complete Medium with Osteogenic Supplement; and Complete Medium with Stromagenic Supplement. Cultures were allowed to incubate in test media for 24 or 48 hours at which points the supernatants were collected, flash frozen in dry ice-ethanol and stored at −70° C. in a Revco freezer until all of the samples were prepared to analyze together. Assays were conducted by applying 100 μl of culture supernatant onto the wells of the ELISA plate followed by processing the plates per manufacturer's instructions. Standard curves were generated using standard cytokines supplied with the kits and diluted to the appropriate concentrations. In some cases (particularly for the IL-6 assay), the supernatants had to be diluted substantially to generate low enough absorbance measurements that could be quantified accurately from the standard curves.

RESULTS

Complete Medium Condition

Detectable levels of six of the nine assayed cytokines were present after 24 hour exposure to constitutive culture-expansion conditions. See FIGS. 12A–12D and 13A–13C and see Tables 7–10 below).

TABLE 7

Detected Cytokine Levels (24 hours)

| Donor | G-CSF 24 h | GM-CSF 24 h | SCF 24 h | LIF 24 h |
|---|---|---|---|---|
| Control | | | | |
| 1 | 15 | 3 | 56 | 52 |
| 2 | 4 | 0 | 53 | 107 |
| 3 | 3 | 0 | 28 | 134 |
| 4 | 0 | 0 | 16 | 7 |
| 5 | 0 | 0 | 30 | 40 |
| 6 | 37 | 0 | 26 | 119 |
| Average | 10 | 1 | 35 | 66 |
| Std.Dev. | 14 | 1 | 16 | 51 |
| OS | | | | |
| 1 | 22 | 0 | 80 | 11 |
| 2 | 0 | 1 | 61 | 20 |
| 3 | 6 | 0 | 34 | 44 |
| 4 | 1 | 0 | 17 | 11 |
| 5 | 4 | 0 | 22 | 11 |
| 6 | 0 | 0 | 34 | 87 |
| Average | 6 | 0 | 41 | 31 |
| Std.Dev. | 8 | 0 | 24 | 30 |
| Pvalue Con:OS | 0.5464 | 0.5761 | 0.1900 | 0.0274 |
| Pvalue OS:SS | 0.0358 | 0.0054 | 0.4714 | 0.0176 |
| IL-1 | | | | |
| 1 | 322 | 527 | 66 | 644 |
| 2 | 966 | 741 | 83 | 622 |
| 3 | 1266 | 413 | 43 | 1008 |
| 4 | 143 | 198 | 28 | 152 |
| 5 | 410 | 307 | 0 | 191 |
| 6 | 164 | 210 | 69 | 338 |
| Average | 545 | 399 | 48 | 493 |
| Std.Dev. | 463 | 209 | 31 | 327 |
| Pvalue Con:SS | 0.038 | 0.0054 | 0.2434 | 0.0180 |

TABLE 8

Detected Cytokine Levels (24 hours)

| Donor | M-CSF 24 h | IL-11 24 h | IL-6 24 h | TGF-β 24 h |
|---|---|---|---|---|
| Control | | | | |
| 1 | 200 | 830 | 7547 | 0 |
| 2 | 233 | 741 | 9887 | 0 |
| 3 | 303 | 659 | 6962 | 0 |
| 4 | 132 | 144 | 6987 | 0 |
| 5 | 130 | 509 | 5384 | 0 |
| 6 | 134 | 343 | 7761 | 0 |
| Average | 178 | 538 | 7421 | 0 |
| Std.Dev. | 70 | 259 | 1467 | 0 |
| OS | | | | |
| 1 | 548 | 0 | 1714 | 0 |
| 2 | 345 | 0 | 338 | 0 |
| 3 | 550 | 52 | 1842 | 0 |
| 4 | 73 | 0 | 650 | 0 |
| 5 | 162 | 9 | 1111 | 0 |
| 6 | 170 | 0 | 919 | 0 |
| Average | 308 | 9 | 1096 | 0 |
| Stan.Dev. | 206 | 21 | 591 | 0 |
| Pvalue Con:OS | 0.1119 | 0.0038 | 0.0004 | |
| Pvalue OS:SS | 0.0123 | 0.0375 | 0.0065 | |
| SS | | | | |
| 1 | 1222 | 3583 | 216666 | 0 |
| 2 | 1355 | 4277 | 255555 | 0 |
| 3 | 2099 | 7351 | 340540 | 0 |
| 4 | 290 | 355 | 76033 | 0 |
| 5 | 753 | 1189 | 109473 | 0 |
| 6 | 589 | 1226 | 122666 | 0 |
| Average | 1051 | 2997 | 186822 | 0 |
| Std.Dev. | 648 | 2620 | 101604 | 0 |
| Pvalue Con:SS | 0.0149 | 0.0569 | 0.0074 | |

TABLE 9

Detected Cytokine Levels (48 hours)

| Donor | G-CSF 48 h | GM-CSF 48 h | SCF 48 h | LIF 48 h |
|---|---|---|---|---|
| Control | | | | |
| 1 | 2 | 0 | 112 | 92 |
| 2 | 0 | 0 | 129 | 123 |
| 3 | 0 | 0 | 41 | 142 |
| 4 | 0 | 0 | 67 | 45 |
| 5 | 0 | 0 | 27 | 28 |
| 6 | 5 | 2 | 38 | 74 |
| Average | 1 | 0 | 69 | 84 |
| Std.Dev. | 2 | 1 | 42 | 44 |
| OS | | | | |
| 1 | 7 | 0 | 98 | 43 |
| 2 | 0 | 0 | 76 | 22 |
| 3 | 2 | 0 | 29 | 26 |
| 4 | 10 | 0 | 100 | 40 |
| 5 | 2 | 0 | 29 | 0 |
| 6 | 0 | 0 | 17 | 8 |
| Average | 4 | 0 | 58 | 23 |
| Std.Dev. | 4 | 0 | 38 | 17 |
| Pvalue Con:OS | 0.3053 | 0.3632 | 0.3901 | 0.0171 |
| Pvalue OS:SS | P.0115 | 0.0027 | 0.1276 | 0.0040 |
| SS | | | | |
| 1 | 452 | 348 | 144 | 841 |
| 2 | 989 | 564 | 162 | 795 |
| 3 | 1214 | 291 | 53 | 866 |
| 4 | 143 | 198 | 28 | 152 |
| 5 | 410 | 307 | 0 | 191 |
| 6 | 164 | 210 | 69 | 338 |
| Average | 545 | 399 | 48 | 493 |
| Std.Dev. | 463 | 209 | 31 | 327 |
| Pvalue Con:SS | 0.038 | 0.0054 | 0.2434 | 0.0180 |

TABLE 10

Detected Cytokine Levels (48 hours)

| Donor | M-CSF 48 h | IL-11 48 h | IL-6 48 h | TGF-β 48 h |
|---|---|---|---|---|
| Control | | | | |
| 1 | 975 | 1414 | 11707 | 0 |
| 2 | 451 | 905 | 10598 | 0 |
| 3 | 632 | 761 | 10691 | 0 |
| 4 | 337 | 225 | 4878 | 0 |
| 5 | 279 | 561 | 4814 | 0 |
| 6 | 222 | 467 | 5645 | 0 |
| Average | 483 | 722 | 8056 | 0 |
| Std.Dev. | 282 | 413 | 3261 | 0 |
| OS | | | | |
| 1 | 867 | 184 | 1230 | 0 |
| 2 | 530 | 0 | 493 | 0 |
| 3 | 655 | 0 | 1395 | 0 |
| 4 | 305 | 0 | 1090 | 0 |
| 5 | 361 | 0 | 1134 | 0 |

TABLE 10-continued

Detected Cytokine Levels (48 hours)

| Donor | M-CSF 48 h | IL-11 48 h | IL-6 48 h | TGF-β 48 h |
|---|---|---|---|---|
| 6 | 264 | 0 | 357 | 0 |
| Average | 497 | 31 | 950 | 0 |
| Std.Dev. | 233 | 75 | 422 | 0 |
| Pvalue Con:OS | 0.6513 | 0.0049 | 0.0029 | |
| Pvalue OS:SS | 0.0114 | 0.0167 | 0.0152 | |
| SS | | | | |
| 1 | 1188 | 4735 | 182352 | 0 |
| 2 | 1416 | 5500 | 36666 | 0 |
| 3 | 1847 | 7351 | 349629 | 0 |
| 4 | 290 | 355 | 76033 | 0 |
| 5 | 753 | 1189 | 109473 | 0 |
| 6 | 589 | 1226 | 122666 | 0 |
| Average | 1051 | 2997 | 186822 | 0 |
| Std.Dev. | 648 | 2620 | 101604 | 0 |
| Pvalue Con:SS | 0.0149 | 0.0569 | 0.0074 | |

The cytokines expressed in terms of pg/10,000 cells in 24 or 48 hours, from lowest to highest were: G-CSF, SCF, LIF, M-CSF, IL-11 and IL-6. Three cytokines were not detected in the supernatants under constitutive culture-expansion conditions: GM-CSF, IL-3 and TGF-β2. Large differences were observed in the average cytokine expression of each cytokine in comparison to the average levels of expression of other cytokines. At the extremes, the average detectable level of G-CSF expression (10 μg/10,000 cells/24 hours) was over 700 fold lower than the average level of expression of IL-6 (7421 pg/10,000 cells/24 hours).

Osteogenic Supplement Culture Conditions

The addition of Osteogenic Supplements to Complete Medium resulted in no detectable changes in G-CSF, M-CSF and SCF relative to control (FIGS. 12A–12D and 13A–13B; Tables 7–10). In contrast, OS medium significantly down-regulated the expression of LIF ($p<0.01$), IL-6 ($p<0.001$) and IL-11 ($p<0.005$) relative to the expression of these cytokines under constitutive culture-expansion medium conditions at 24 hours. These levels remained statistically lower than cytokine levels in constitutive culture-expansion medium conditions at 48 hours (FIGS. 12A–12D and 13A–13C; Tables 7–10). The amount of OS medium-mediated inhibition varied for the three cytokines; at the 24 hour timepoint the average level of cytokine expression in OS-medium relative to constitutive culture-expansion medium conditions was as follows; LIF expression 55%±54%, IL-6 16%±9% and IL-11 1%±3%. The large standard deviation in the LIF percent change was due primarily to the measurements from one donor (donor #4) where the level of LIF expression was actually higher under OS medium conditions relative to constitutive culture-expansion conditions (Table 7). For a given donor, the percent inhibition of a cytokine relative to the average absolute level of inhibition of that cytokine, was independent to the percent inhibition of the other two cytokines, relative to their average absolute levels of inhibition (Tables 7–10). In addition, for each of the cytokines, the percent inhibition for a given cytokine among the six individuals in the population, was independent of the initial levels of expression under constitutive culture-expansion conditions (FIGS. 12A–12D and 13A–13C; Tables 7–10).

Stromagenic Supplement Culture Conditions

SS medium increased the expression of several cytokines by MSCs in a concentration dependent manner. FIG. 14 illustrates the 24 hour response of second passage MSCs to increasing concentrations of IL-1α in terms of expression of GM-CSF. There is a near linear increase in the level of GM-CSF secretion by MSCs, with increasing levels of IL-1α in the culture medium between 0.1–10.0 U/ml. Additional log increases in IL-1α to the culture medium results in little additional increase in GM-CSF expression. These data were used to identify the concentration of IL-1α to supplement to the culture media in the experiments described below. For all subsequent assays, 10 U/ml IL-1α were added to the culture media.

Culture medium supplemented with 10 U/ml IL-1α induced statistically significant up-regulation in the expression of G-CSF ($P<0.05$), M-CSF ($p<0.02$), LIF ($p<0.02$), IL-6 ($p<0.01$) and IL-11 ($p<0.06$) relative to cells cultured in constitutive culture-expansion medium. In addition, IL-1α induced the expression of GM-CSF which was not detectable in constitutive culture-expansion medium. In contrast, IL-1α had no statistically significant effect on the expression of SCF relative to the level of expression under constitutive culture-expansion medium conditions. The fold increase in response to IL-1α varied depending on the cytokine. IL-6 (25.1+/−13.4 fold increase) was stimulated to the greatest extent, followed by LIF (9.2±6.9 fold), M-CSF (5.2±1.7 fold) and IL-11 (4.9±3.3 fold). The average fold increase for G-CSF and GM-CSF were not calculated, since these cytokines were not detected in some or all constitutive culture-expansion cultures.

DISCUSSION

Our continued analyses of MSCs in this study were aimed at identifying additional phenotypic characteristics, and determining how this phenotype is altered when MSCs are exposed to regulatory molecules that cause differentiation or phenotypic modulation. In this study, we used ELISA assays to characterize the cytokine expression of MSCs under constitutive culture-expansion conditions, and in the presence of OS or SS.

MSCs express a unique profile of cytokines which include G-CSF, M-CSF, SCF, LIF, IL-6 and IL-11 under constitutive culture-expansion conditions. They do not express GM-CSF, IL-3 and TGF-β2 under these conditions. OS down-regulates the expression of LIF, IL-6 and IL-11, while not affecting the expression of the other cytokines expressed under constitutive culture conditions. OS was not observed to up-regulate the expression of any of the cytokines assayed in this study. In contrast, SS up-regulates the expression of G-CSF, M-CSF, LIF, IL-6 and IL-11, and induces the expression of GM-CSF which was not detected under constitutive culture-expansion conditions. SS had no effect on SCF expression, and was not observed to down-regulate any of the cytokines assayed in this study. Through these data, a unique cytokine expression profile has been generated that can aid in distinguishing MSCs from other mesenchymal phenotypes. The identity of the cytokine profile should provide clues to determine the role that these cells play in the microenvironment of bone marrow which provides the inductive and regulatory information that supports hematopoiesis. In addition, the alterations in this cytokine profile in response to OS and SS, identify specific cytokines whose levels of expression change as MSCs differentiate or modulate their phenotype in response to regulatory molecules.

IL-1α, which is released in the marrow microenvironment by a variety of cell types during inflammatory responses, induces MSCs to up-regulate expression of cytokines that support granulocytic (G-CSF and GM-CSF), monocytic/osteoclastic (GM-CSF, LIF, M-CSF, IL-6) and megakaryocytic (IL-11) differentiation. IL-1α has been shown to protect bone marrow from radio- and hemo-ablation. The IL-1α-induced up-regulation of cytokine expression by MSCs likely plays a role in the mechanisms of IL-1α's protective effects.

Dexamethasone, which induces MSCs to differentiate into osteoblasts, attenuates the expression of monocytic/osteoclastic (LIF, IL-6) and megakaryocytic (IL-11) supportive cytokines, and has no effect on the expression of cytokines that support granulocytic progenitors (G-CSF, A GM-CSF). The three cytokines inhibited by dexamethasone are of interest because each mediates its signal through a receptor that uses gp130 in its signaling pathway.

Cited Literature

1. Caplan AI, In: 39*th Annual Symposium of the Society for Developmental Biology*, ed by S. Subtelney and U Abbott, pp 3768. New York, Alan R Liss Inc, 1981.
2. Elmer et al., *Teratology*, 24:215–223, 1981.
3. Hauschka SD, *Dev Biol*, 37:345–368, 1974.
4. Solursh et al., *Dev Biol*, 83:9–19, 1981.
5. Swalla et al., *Dev Biol*, 116:31–38, 1986.
6. Goshima et al., *Clin Orthop Rel Res*, 269:274–283, 1991.
7. Ashton et al., *Clin Orthop Rel Res*, 151:294–307, 1980.
8. Bruder et al., *Bone Mineral*, 11:141–151, 1990.
9. Bennett et al., *J Cell Sci*, 99:131–139, 1991.
10. Benayahu et al., *J Cell Physiol*, 140:1–7, 1989.
11. Nakahara et al., *Exp Cell Res*, 195:492–503, 1991.
12. Dennis et al., *Cell Transpl*, 1:2332, 1991.
13. Ohgushi, et al., *Acta Scandia.*, 60:334–339, 1989.
14. Wang et al., *Growth Factors*, 9:57, 1993.
15. Vukicevic et al., *PNAS*, 86:8793, 1989.
16. Cheng et al., *Endocrinology*, 134:277, 1994.
17. Tenenbaum et al., *Calcif. Tissue Int.*, 34:76, 1982.
18. Bruder et al., *Trans. Ortho. Res. Soc.*, 16:58, 1991.
19. Leonard et al., *Devl. Biol.*, 145:99, 1991.
20. Chen et al., *Exp. Cell Res.*, 206:199, 1993.
21. Syftestad et al., *Differentiation*, 29:230, 1985.
22. Chen et al., *Exp. Cell Res.*, 195:509, 1991.
23. Kimura et al., *Biomed. Res.*, 5:465, 1984.
24. Langille et al., *Differentiation*, 40:84, 1989.
25. Russell et al., *Exp. Hematol.*, 20:75–79, 1992.
26. Brenner et al., *Brit. J. of Haem.*, 77:237–244, 1991.
27. Haynesworth, et al., *Bone*, 13:81–88, 1992.
28. Grigoriadis, et al., *J. Cell Biol.*, 106:2139–2151, 1988.
29. Haynesworth, et al., *Bone*, 13:69–80, 1992.
30. Bruder & Haynesworth, in preparation.
31. Bruder & Caplan, *Dev. Biol.*, 141:319–329, 1990.
32. Pacifici, et al., *Exp. Cell Res.*, 195:38, 1991.
33. Constantinides et al., *Nature*, 267:364–366, 1977.
34. Taylor et al., *Cell*, 17:771–779, 1979.
35. Konieczny et al., *Cell*, 38:791–800, 1984.
36. Lassar, *Cell*, 47:649–656, 1986.

What is claimed is:

1. A composition for inducing lineage-directed differentiation of isolated human mesenchymal stem cells into a single particular mesenchymal lineage, which comprises human mesenchymal stem cells and one or more bioactive factors for inducing differentiation of the mesenchymal stem cells into a single particular lineage.

2. The composition of claim 1 wherein the composition comprises a mixture of bioactive factors.

3. The composition of claim 1 wherein the bioactive factor induces differentiation of isolated human mesenchymal stem cells into a mesenchymal lineage selected from the group consisting of osteogenic, chondrogenic, tendonogenic, ligamentogenic, myogenic, marrow stromagenic, adipogenic and dermogenic.

4. The composition of claim 1 further comprising a pharmaceutically acceptable carrier.

5. The composition of claim 4 wherein the carrier is an injectable liquid.

6. The composition of claim 4 wherein the carrier is a rigid porous vessel.

7. The composition of claim 4 wherein the carrier is a gel.

8. The composition of claim 1 wherein the bioactive factor is an osteoinductive factor for inducing osteogenic lineage differentiation of the human mesenchymal stem cells.

9. The composition of claim 8 wherein the osteoinductive factor is a bone morphogenic protein.

10. The composition of claim 9 wherein the bone morphogenic protein is selected from the group consisting of BMP-2 and BMP-3.

11. The composition of claim 8 wherein the osteoinductive factor is a fibroblast growth factor.

12. The composition of claim 11 wherein the fibroblast growth factor is basic fibroblast growth factor.

13. The composition of claim 8 wherein the osteoinductive factor is a glucocorticoid.

14. The composition of claim 13 wherein the glucocorticoid is dexamethasone.

15. The composition of claim 8 wherein the osteoinductive factor is a prostaglandin.

16. The composition of claim 15 wherein the prostaglandin is prostaglandin E1.

17. The composition of claim 8 which further comprises contacting the isolated human mesenchymal stem cells with an adjunct factor.

18. The composition of claim 17 wherein the adjunct factor is selected from the group consisting of ascorbic acid and its analogs and a glycerophosphate.

19. The composition of claim 1 wherein the bioactive factor is a chondroinductive factor for inducing chondrogenic lineage differentiation of the human mesenchymal stem cells.

20. The composition of claim 19 wherein the chondroinductive factor is a member of the transforming growth factor-β superfamily.

21. The composition of claim 20 wherein the transforming growth factor-β superfamily member is TGF-β1.

22. The composition of claim 20 wherein the transforming growth factor-β superfamily member is inhibin A.

23. The composition of claim 20 wherein the transforming growth factor-β superfamily member is chondrogenic stimulating activity factor.

24. The composition of claim 20 wherein the transforming growth factor-β superfamily member is a bone morphogenic protein.

25. The composition of claim 24 wherein the bone morphogenic protein is BMP-4.

26. The composition of claim 19 wherein the chondroinductive factor is a component of the collagenous extracellular matrix.

27. The composition of claim 26 wherein the collagenous extracellular matrix component is collagen I.

28. The composition of claim 27 wherein the collagen I is in the form of a gel.

29. The composition of claim 19 wherein the chondroinductive factor is a vitamin A analog.

30. The composition of claim 29 wherein the vitamin A analog is retinoic acid.

31. The composition of claim 1 wherein the bioactive factor is a stromainductive factor for inducing stromagenic lineage differentiation of the human mesenchymal stem cells.

32. The composition of claim 31 wherein the stromainductive factor is an interleukin.

33. The composition of claim 32 wherein the interleukin is selected from the group consisting of interleukin-1α and interleukin-2.

34. The composition of claim 1 wherein the bioactive factor is a myoinductive factor for inducing myogenic lineage differentiation of the human mesenchymal stem cells.

35. The composition of claim 34 wherein the myoinductive factor is a cytidine analog.

36. The composition of claim 35 wherein the cytidine analog is selected from the group consisting of 5-azacytidine and 5-aza-2'-deoxycytidine.

* * * * *